US011984222B2

(12) United States Patent
Burbank et al.

(10) Patent No.: US 11,984,222 B2
(45) Date of Patent: May 14, 2024

(54) SYSTEM AND METHOD FOR SHARING HEALTH DATA

(71) Applicant: Safety Shield Products, LLC, Sanford, FL (US)

(72) Inventors: William Burbank, Sanford, FL (US); Tom Benstein, Delray Beach, FL (US)

(73) Assignee: Safety Shield Products, LLC, Sanford, FL (US)

(*) Notice: Subject to any disclaimer, the term of this patent is extended or adjusted under 35 U.S.C. 154(b) by 214 days.

(21) Appl. No.: 17/560,172

(22) Filed: Dec. 22, 2021

(65) Prior Publication Data

US 2023/0061616 A1 Mar. 2, 2023

Related U.S. Application Data

(63) Continuation-in-part of application No. 17/465,041, filed on Sep. 2, 2021, now abandoned.

(51) Int. Cl.
*G16H 40/67* (2018.01)
*G08B 21/18* (2006.01)
(Continued)

(52) U.S. Cl.
CPC ............. *G16H 40/67* (2018.01); *G16H 10/60* (2018.01); *G16H 50/30* (2018.01); *H04N 7/186* (2013.01); *G08B 21/18* (2013.01)

(58) Field of Classification Search
CPC ........ G16H 40/67; G16H 10/60; G16H 50/30; H04N 7/186
(Continued)

(56) References Cited

U.S. PATENT DOCUMENTS 7,899,218 B2 3/2011 Satoshi
8,041,016 B2 * 10/2011 Trell .................... H04M 11/025 455/420
(Continued)

FOREIGN PATENT DOCUMENTS

KR 10-2169082 B1 10/2020
KR 10-2220469 B1 2/2021
WO 2011005224 A1 1/2011

OTHER PUBLICATIONS

Korean Intellectual Property Office, International Search Report issued in PCT/US2022/074809 (Nov. 23, 2022).
(Continued)

*Primary Examiner* — Maria El-Zoobi
(74) *Attorney, Agent, or Firm* — Finch & Maloney PLLC

(57) ABSTRACT

Disclosed are systems and methods for sharing health information. For example, the system includes a sensor unit adjacent a building entrance, a first computing device of a visitor to the building entrance, and a second computing device associated with an occupant of the building. The system can include device connected to a smart-home network. One method includes detecting the first computing device adjacent the entrance, requesting health data from the first computing device, the first computing device checking for authorization to share the health data with a user associated of the second computing device; the first computing device sending health data to the second computing device, a second computing device receiving the health data pertaining to the user of the first computing device, and the second computing device notifying the user of the second computing device based on the received health data.

17 Claims, 18 Drawing Sheets

(51) Int. Cl.
*G16H 10/60* (2018.01)
*G16H 50/30* (2018.01)
*H04N 7/18* (2006.01)

(58) Field of Classification Search
USPC .............................................................. 705/3
See application file for complete search history.

(56) References Cited

U.S. PATENT DOCUMENTS 8,526,780 B2 9/2013 Weisbach
8,903,317 B2 12/2014 Wu
8,918,162 B2 12/2014 Prokoski
9,247,219 B2 1/2016 Kasmir et al.
9,253,455 B1 * 2/2016 Harrison .............. H04M 11/025
9,342,936 B2 5/2016 Scalisi
9,734,675 B2 8/2017 Siminoff
9,819,867 B2 11/2017 Siminoff et al.
9,924,078 B2 3/2018 Wieser
9,948,892 B2 4/2018 Siminoff et al.
9,978,254 B2 5/2018 Siminoff et al.
10,009,520 B2 6/2018 Siminoff
10,070,058 B2 9/2018 Siminoff et al.
10,217,331 B2 2/2019 Siminoff
10,270,971 B2 4/2019 Siminoff et al.
10,499,011 B2 12/2019 Siminoff et al.
10,506,205 B2 12/2019 Siminoff et al.
10,554,887 B2 2/2020 Siminoff et al.
10,629,063 B2 4/2020 Siminoff et al.
10,635,907 B2 4/2020 Child et al.
10,666,913 B1 5/2020 Siminoff
10,674,119 B2 6/2020 Scalisi et al.
10,777,057 B1 9/2020 Siminoff
10,783,757 B2 9/2020 Siminoff
10,904,492 B2 1/2021 Derenne et al.
10,923,216 B1 2/2021 White et al.
10,939,040 B2 3/2021 Siminoff et al.
10,991,185 B1 4/2021 Luthra et al.
10,999,505 B2 5/2021 Siminoff et al.
11,011,003 B1 5/2021 Jafri et al.
2012/0320215 A1 12/2012 Maddi
2013/0045763 A1 2/2013 Ruiz
2013/0054271 A1 2/2013 Langford et al.
2017/0048489 A1 2/2017 Carter
2017/0239524 A1 * 8/2017 Lee ........................ G16H 50/30
2019/0304274 A1 10/2019 Britton et al.
2020/0288045 A1 9/2020 Jeong et al.
2020/0293768 A1 9/2020 Ogura
2021/0104145 A1 * 4/2021 Wakita ................... H04R 27/00
2021/0183278 A1 * 6/2021 Lai ........................ H04W 88/04
2021/0302427 A1 9/2021 Stone
2021/0304537 A1 * 9/2021 Reed ....................... G06F 18/22
2021/0304901 A1 9/2021 Pal
2021/0319863 A1 10/2021 Rajagopal et al.
2021/0326474 A1 10/2021 Sparks et al.
2021/0327548 A1 * 10/2021 Sparks ................. A61B 5/1172
2021/0335072 A1 10/2021 Caldwell et al.
2022/0031258 A1 * 2/2022 Xing ...................... A61B 5/742
2023/0067950 A1 * 3/2023 Burbank .................. G08B 3/10

OTHER PUBLICATIONS

Lance Whitney, 12 Ways to Get Healthy With Your Apple Watch, PCMag, Dec. 14, 2021, available at https://www.pcmag.com/how-to/get-healthy-with-your-apple-watch?.

Chandra Steele, Does My State Have a COVID-19 Vaccine App?, PCMag, Dec. 3, 2021, available at https://www.pcmag.com/how-to/does-my-state-have-a-covid-19-vaccine-app?.

Micro-Epsilon, "Thermal imaging camera for body temperature monitoring", www.micro-epsilon.com/temperature-sensors/thermoIMAGER/ (downloaded Jul. 22, 2021).

US Food and Drug Administration, "Thermal Imaging Systems (Infrared Thermographic Systems / Thermal Imaging Cameras)," www.fda.gov/medical-devices/general-hospital-devices-and-suppl (downloaded Jul. 22, 2021).

US Patent and Trademark Office, Non-Final Office Action issued in U.S. Appl. No. 17/465,041 (Sep. 23, 2022).

Polley, John C. et al., On an innovative architecture for digital immunity passports and vaccination certificates, arXiv preprint arXiv:2103.04142, Retrieved at https://arxiv.org/ftp/arxiv/papers/2103/2103.04142.pdf (Mar. 6, 2021).

Huang, Lu et al., Research on Internet of Things Technology and its Application in Building Smart Communities, 1550 J. Physics: Conference Series 022029 (2020) (available at https://iopscience.iop.org/article/10.1088/1742-6596/1550/2/022029/pdf).

* cited by examiner

SYSTEM AND METHOD FOR SHARING HEALTH DATA

RELATED APPLICATIONS

This application is a continuation-in-part of U.S. patent application Ser. No. 17/465,041 titled NON-CONTACT BODY TEMPERATURE SYSTEM AND METHOD and filed on Sep. 2, 2021, the contents of which are incorporated herein by reference in its entirety.

TECHNICAL FIELD

The present disclosure relates generally to wireless communication between electronic devices, and more specifically to a system and method for sharing health information between the electronic devices of various users.

BACKGROUND

Video doorbells enable a homeowner to view and communicate with a visitor at the door. For example, by activation via a motion sensor or when the visitor presses the doorbell, a video doorbell turns on to capture video of the area in front of the doorbell. The owner receives an alert on a mobile phone or smart display and can view video of the visitor(s) in real time, whether a salesman, burglar, package delivery person, animal, neighbor, or family member, for example. Upon viewing the alert and/or video, the homeowner can speak to the visitor, admit the visitor to the property, or ignore the alert as appropriate for a given situation. Some such video doorbells are equipped with motion detection, wireless two-way audio communication, wireless video transmitted to a phone or other device, and real-time notification.

SUMMARY

One aspect of the present disclosure is directed to systems and methods of determining and/or sharing health information between a visitor to a building entrance and the building occupant, such as for screening the visitor prior to granting entry to the building.

In one example, a temperature of a visitor at a building entrance can be determined using a system equipped with a sensor unit positioned adjacent a building entrance. In another example, a system enables sharing health data of the visitor communicated from the visitor's computing device to the occupant's computing device. Numerous variations and embodiments will be apparent in light of the present disclosure.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes and not to limit the scope of the disclosed subject matter.

Figure 1:
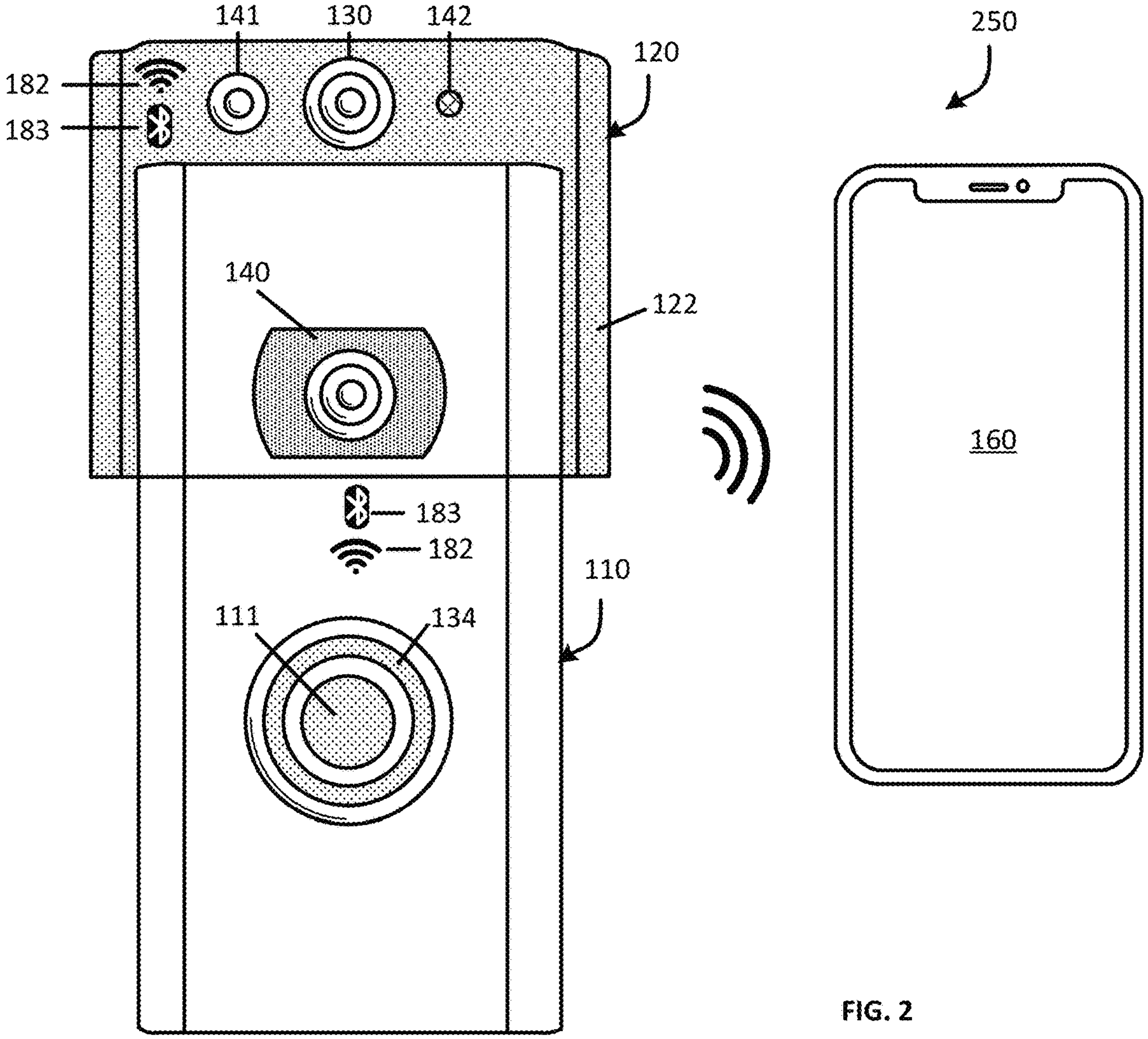
FIG. 1 illustrates a front perspective view of a video doorbell assembly and a temperature sensor unit coupled together, in accordance with an embodiment of the present disclosure.

The figures depict various embodiments of the present disclosure for purposes of illustration only. Numerous variations, configurations, and other embodiments will be apparent from the following detailed discussion.

DETAILED DESCRIPTION

General Overview

Video doorbells and home security systems allow the user to identify and communicate with visitors to a building entrance or other access point. However, these systems do not provide any information to the building occupant about the visitor's health. Body temperature, vaccination status, and other health information can give a homeowner or dwelling occupant, peace of mind by providing much-needed health information about the visitor that can be used to avoid potential exposure to COVID-19 and other illnesses. In particular, it would be desirable for a homeowner or other building occupant to be able to screen visitors for the purpose of reducing exposure to disease, such as COVID-19. It would also be desirable for a building occupant to be informed of the visitor's body temperature or other health conditions by receiving a notification on a computing device when a visitor approaches the entrance. To address these needs and others, and in accordance with some embodiments of the present disclosure, systems and methods in accordance with some embodiments of the present disclosure enable a building occupant to screen a visitor to the building entrance based on health data of the visitor relayed to the occupant's computing device.

In accordance with some embodiments, the building occupant can receive a notification on a computing device (e.g., phone, tablet, smart display, smart speaker, etc.) when a visitor approaches the entrance. After detecting the visitor, for example, the system can acquire body temperature of the visitor, or the system can relay shared health information to the building occupant. Accordingly, the building occupant can screen visitors using health information shared between the visitor and the building occupant via the visitor's and the occupant's respective electronic devices.

In one example, a temperature sensor is configured to detect the body temperature of a visitor, followed by the system communicating that temperature information to the user's computing device, such as by displaying a value on the user's smart phone, smart display, or computer. In one such embodiment, the system includes a temperature sensor unit adjacent the building entrance, and a computing device in communication with the temperature sensor unit. When a visitor arrives at the entrance, the temperature sensor unit detects the visitor's body temperature and relays the temperature information to the user's computing device to be displayed to the user. In other embodiments, the temperature sensor can be part of a wearable device on the visitor's person, such as a fitness tracker or smart watch that communicates data to the visitor's computing device. After approaching the entrance, the visitor's computing device acquires data from the wearable device and shares that data with the building occupant.

In some embodiments, the system can include or can operate with an existing video doorbell assembly, such as one equipped with an optical camera, microphone, and communications capabilities. In one example, the system includes the video doorbell assembly with an optical camera, a microphone, and a speaker, and which is configured to communicate with the building occupant's computing device or smart home network. A sensor unit adjacent the entrance is configured to detect an approaching visitor, such as by detecting an audible chime resulting from the visitor pressing the doorbell button on a video doorbell assembly, a motion sensor detecting movement of a visitor approaching the entry, or a sensor detecting the computing device (e.g., phone) of a visitor based on RFID or Bluetooth communication with the visitor's computing device. Upon detecting the visitor at the entrance, the system alerts the building occupant with a notification on the user's computing device.

In some embodiments, the sensor unit can determine the body temperature of the visitor and the system displays that information to the user on the user's computing device. The system can further enable communication between the building occupant and the visitor using the occupant's computing device and the video doorbell assembly's optical camera, microphone, and speaker. The sensor unit can communicate directly or indirectly with other system devices. The system can use an application programming interface (API) to communicate between the user's computing device, the video doorbell assembly or sensor unit, a networked computer, and the visitor's computing device.

In some embodiments, software of an existing video doorbell or security system can be modified or used in conjunction with system software to display temperature or other health information on the building occupant's computing device, and to utilize the communications capabilities (e.g., speaker, microphone, and video camera) of the video doorbell assembly for communication between the occupant and the visitor. Accordingly, the user interface on the computing device can be used to communicate with the visitor using the existing video doorbell assembly in addition to displaying and/or processing body temperature information received from the temperature sensor unit.

In another example, a doorbell system includes a temperature sensor unit, such as an infrared (IR) sensor or camera, that can be triggered by a motion sensor or some other event. Alternately, the temperature sensor can be a stand-alone unit, a temperature sensor that is part of a wearable device of the visitor, or part of an accessory to an existing video doorbell assembly, for example. After detecting a visitor event, such as a visitor pressing the doorbell button or the visitor being detected by a motion detector, the temperature sensor determines the visitor's body temperature, whether a single point reading or by acquiring a temperature map of objects in view of a thermal imaging camera, for example. The temperature data captured by the temperature sensor can be communicated to the user's computing device. In some embodiments, after receiving an alert that a visitor is at the door, the user can proceed to select a particular region or point of interest within a field of view to be analyzed for temperature information. In one example, a processor analyzes a thermal image or video to determine temperature data, such as high and low temperatures or the temperature data within a particular region in the field of view. In another example, the temperature sensor detects the temperature at a location on the visitor's body that is selected by the user.

In other embodiments, the optical camera of the doorbell assembly can be enabled or configured to scan machine-readable code, such as a barcode, 2D barcode (e.g., a QR code), or other machine-readable graphical representation displayed on the visitor's computing device, where the machine-readable code contains health information, such as a vaccination record. For example, the building occupant can install system software on his/her computing device that enables the optical camera of the existing doorbell assembly to scan and process a 2D barcode. Some such system software can enable an existing video doorbell camera to read and share health data from the visitor's 2D barcode, enable the camera of a separate add-on component to the doorbell assembly to read and process a 2D barcode, or enable a separate (e.g., stand-alone) optical camera or barcode reader located outside the building entrance to read and process a 2D barcode. In one example, after receiving the information from the sensor unit that a visitor is at the door, the system notifies the building occupant. After being prompted to do so, the visitor can position a 2D barcode displayed on his/her computing device within the field of view of the camera unit, which scans and processes the barcode. The system then notifies the building occupant of the visitor's health and/or vaccination status based on data contained in the barcode.

In accordance with another embodiment of the present disclosure, system is configured to communicate health information from a computing device of a visitor to a computing device of a building occupant either directly (e.g., peer-to-peer device transfer) or indirectly (e.g., via a server computer or network hub). In such embodiments, no doorbell assembly is required, although one can optionally be included as part of a smart home system, for example. In one such embodiment, a sensor unit adjacent the building entrance is configured to detect a visitor's computing device as the visitor approaches the building entrance. For example, the sensor unit can communicate with a visitor's computing device via Bluetooth, Wi-Fi, near-field communication, or RFID technology. Communication between the sensor unit and the visitor's computing device, such as via system software running on the respective devices, enables the sensor unit to detect the presence of the computing device, or vice versa. Such communication can include RFID or near-field communication, Bluetooth, or Wi-Fi communication to name a few examples.

Depending on how system software is configured on the visitor's and the building occupant's respective devices, the visitor's computing device may automatically share health information with the building occupant's device. Alternately, the visitor may be prompted for user input upon approaching the building entrance. System users can establish personal contacts with whom share rules are established in the system software. For example, the visitor's software is pre-authorized to share certain health data with other identified users of the system software, such as friends and family. In such an embodiment, the sensor unit (or the visitor's computing device) can send a notification to the computing device of the building occupant, informing the occupant that a known visitor (e.g., pre-checked visitor, or verified visitor) is at the entrance. Based on established sharing preferences, the system provides the occupant with the shared health information via a notification to the occupant's computing device. In another embodiment, such as when the visitor and occupant are not established personal connections in the system software, the system can detect the presence of a compatible computing device when the visitor approaches the building entrance. The visitor can then be prompted to share health information, such as vaccination status, answers to a screening questionnaire, or data accessed from or via a smart health app on a smart phone or wearable device. Based on the visitor's input to the computing device (e.g., to either deny the request or to authorize sharing health information), a notification is presented to the building occupant via the occupant's computing device.

In some embodiments, system users can establish communication between a wearable device and a computing device in order to acquire health data from the wearable devices in real time, such as pulse rate and body temperature, and communicate that information to the building occupant using the system. System users can further establish authorizations for the system to acquire health information from other sources, such as an employer human resources database, a medical practitioner database, or some other database accessible via an Internet connection.

In one such embodiment, the system is a smart home system that includes one or more computing devices of the building occupant, such as mobile phone(s), personal computer(s), smart speaker(s), television(s), and a network hub. The smart home network can communicate with a visitor's computing device that also is running system software. In some embodiments, the system may utilize a cloud-based computer, such as a server computer, to relay messages between devices and/or to process information. Further, a system can be configured to operate with an existing device, such as a video doorbell assembly or security system. Such a system enables a building occupant to screen visitors based on shared health information via communication (e.g., Wi-Fi or cellular) between the visitor's computing device and the building occupant's smart home network.

Systems and methods in accordance with embodiments of the present disclosure can be used by a building occupant to screen visitors based on health information shared between computing devices. The health information can be stored on a visitor's computing device, can be acquired in real time from system devices, or can be acquired from another database via an Internet connection, for example. Some such systems can be used at an entrance to a building, such as a home, business, medical office, public building, or other building where the occupant wishes to know the health status of the person seeking entry. Numerous variations and embodiments will be apparent in light of the present disclosure.

Example Embodiments

FIG. 1 illustrates a front perspective view of a doorbell assembly 110, a sensor unit 120, and a computing device 160 as components of a system 250, in accordance with an embodiment of the present disclosure. The doorbell assembly 110 and sensor unit 120 are part of a system 250 that also includes a computing device 160 in communication with the doorbell assembly 110 and/or the sensor unit 120. The computing device 160 can be a smartphone, a tablet computer, a personal computer, a smart display, a television, a smart watch, or other wired or wireless computing device. In one example, the computing device 160 is a portable Internet-enabled electronic product that includes a display screen, speaker, microphone, and camera, and that enables the user to interact with other Internet-enabled devices, cell phones, security devices, and the like. Examples of a smart display include the electronic products sold as the Amazon Echo, Amazon Alexa, Google Home Mini.

The doorbell assembly 110 is configured as a video doorbell assembly and includes a doorbell button 111, a microphone/speaker 134, and an optical camera 140. The doorbell assembly 110 is equipped with a Wi-Fi transceiver 182 for wireless communication with the user's computing device 160. In some embodiments, the doorbell assembly 110 includes a Bluetooth transceiver 183.

In this example, the sensor unit 120 is mounted to the doorbell assembly 110 and includes a temperature sensor 130. For example, the housing 122 of the sensor unit 120 is shaped to mate with or to otherwise be mounted on or over the doorbell assembly 110. The sensor unit 120 includes a housing 122 that retains a temperature sensor 130, such as a thermal imaging camera, and associated circuitry needed to detect a body temperature, whether at a single point or a temperature map within a field of view of the temperature sensor 130. One such temperature sensor 130 is an infrared camera configured to capture video and/or still images. Optionally, the sensor unit 120 includes an optical camera 141 and/or an ambient temperature sensor 142. For example, the optical camera 141 can be used for facial recognition and/or to display a view of the temperature sensor 130 to the user. The ambient temperature sensor 142 can be a thermocouple, digital thermometer, or other component configured to detect ambient temperature in the nearby region of the sensor unit 120.

In some embodiments, the sensor unit 120 is configured to communicate directly or indirectly with the doorbell assembly 110 via wired or wireless means. In one example, the sensor unit 120 has a wired connection to the doorbell assembly 110. In another example, the sensor unit 120 may include one or both of a Bluetooth transceiver 183 and a Wi-Fi transceiver 182. For example, the sensor unit 120 uses the Bluetooth transceiver 183 for communication with the doorbell assembly 110 and with the user's computing device 160 at short range, such as when the user is at home. The sensor unit 120 can use the Wi-Fi transceiver 182 for communicating with the user's computing device 160 when the user is away from the dwelling. For example, the temperature sensor unit 120 joins the residence's (or building's) local Wi-Fi network to communicate with the resident's computing device 160 via the network's wireless router. For example, the local Wi-Fi network can be a wireless network of a home or business and includes a wireless router. The local Wi-Fi network typically is within the building housing the entrance where entry is sought, but the system can also use a nearby wireless network in some embodiments.

In some embodiments, the sensor unit 120 is a temperature sensor unit configured to wirelessly communicate captured temperature information to the user's computing device 160 using cloud-based software and a wireless communications protocol, such as IEEE 802.11 for Wi-Fi communications or near-field communication. In some embodiments, the system 250 includes a microphone 134, a Bluetooth transceiver 183, and a power source. The power source can be a rechargeable lithium-ion battery, replaceable batteries, or wiring to a mains power supply, a solar panel, or other suitable power source. In some embodiments, the system 100 includes an optical camera 141 on the sensor unit 120 and/or an optical camera 140 that is part of a doorbell assembly, where the optical camera 140/141 is suited to capture video and/or still images. In some embodiments, the optical camera 140/141 can be used to capture images or video that are processed by the processor 148 to detect a face or facial region. In some embodiments, the optical camera 140 of the video doorbell can be configured or enabled to capture a 2D barcode (e.g., a QR code) that contains health information. For example, the 2D barcode includes data acquired from a wearable device on the visitor, data stored on the visitor's computing device, data acquired using a Smart Health App, or a link to a database accessible over the Internet. In some embodiments, the system 100 includes an ambient temperature sensor 142, such as a digital thermometer or thermocouple.

System 250 includes a processor 148 configured to processes images, video, or temperature data captured by the temperature sensor 130 and/or the optical camera 140/141. The processor can be cloud-based software or hardware (e.g., a server computer "in the cloud"), the user's computing device, firmware and/or hardware in the sensor unit 120, or a combination thereof. After capturing temperature information or detecting the visitor's body temperature, for example, the processor 148 within the sensor unit 120 processes the raw captured data. The processor 148 can also or alternately be configured to process a 2D barcode captured by the optical camera 141 of the sensor unit 120 or optical camera 140 of the video doorbell assembly 110. Processing may additionally or alternately be performed by a server computer "in the cloud," by the user's computing device 160, or a combination of such devices.

In some embodiments, the system 250 is configured to determine whether the visitor's facial area is covered by a mask or clothing, and during processing excludes covered areas of the facial region from a "hot spot" in the temperature measurement region. Determining face covering can be performed, for example, by detecting a facial region of the visitor and analyzing the temperature measurements of the facial region. If the temperature gradients within the facial region deviate more than a predetermined amount with temperature gradients of an uncovered facial region stored in the system, the system 250 identifies one or more facial coverings. For example, if a visitor's is completely covered or covered to the extent that a reliable temperature measurement cannot be obtained (e.g., visitor wearing a hat, sunglasses, and mask covering the nose and lower face), the system 250 alerts the user of this condition. Optionally, the system 250 prompts the user to communicate with the visitor to remove some or all of the face covering.

Figure 2:
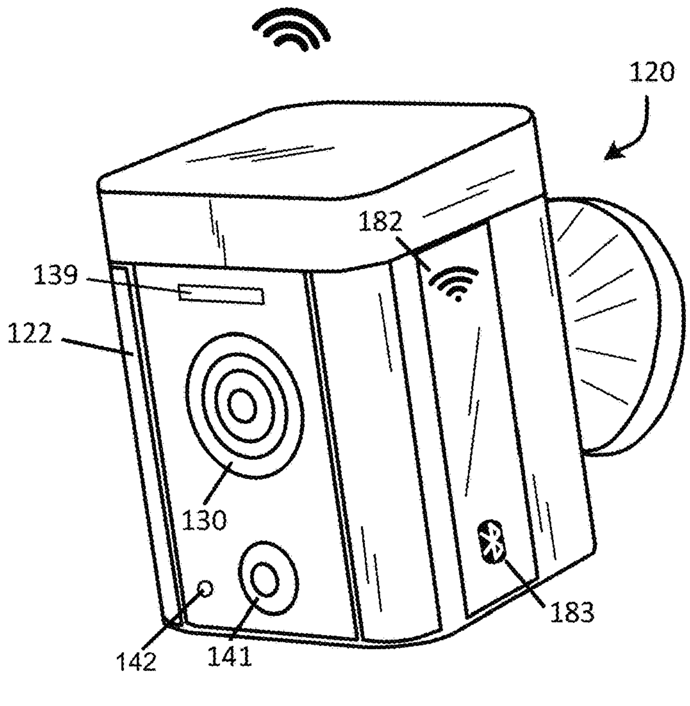
FIG. 2 illustrates a temperature sensor unit that can be mounted to a wall or other surface adjacent an entry point, in accordance with an embodiment of the present disclosure.

FIG. 2 illustrates a sensor unit 120 that can be mounted to an outside wall adjacent to a door or other entrance, in accordance with an embodiment of the present disclosure. For example, the sensor unit 120 can be mounted within a range of 10 meters of a building entrance, including within 3 meters, within 1 meter, within 0.5 meter, and within 0.1 meter. In some embodiments, the sensor unit 120 includes a temperature sensor 130, such as a thermal imaging camera or other suitable device for detecting the body temperature of a visitor. The sensor unit 120 can additionally or alternately include one or more of a motion sensor 139, RFID transceiver, optical camera 141, ambient temperature sensor 130, or other sensor. Similar to the embodiment shown in FIG. 1, the sensor unit 120 of FIG. 2 optionally can include an optical camera 140, ambient temperature sensor 142, microphone 134, Bluetooth transceiver 183, Wi-Fi transceiver 182, and/or a motion sensor, as deemed appropriate for a given application. When mounted separately from the doorbell assembly 110, for example, the sensor unit 120 optionally can be configured to communicate directly or indirectly with the doorbell assembly 110 using wireless means (e.g., Bluetooth transceiver 183), although a wired connection can also be used. In other embodiments, the sensor unit 120 is triggered by motion or sound. In some such embodiments, the sensor unit 120 operates independently of the doorbell assembly 110 (if present).

Figure 3:
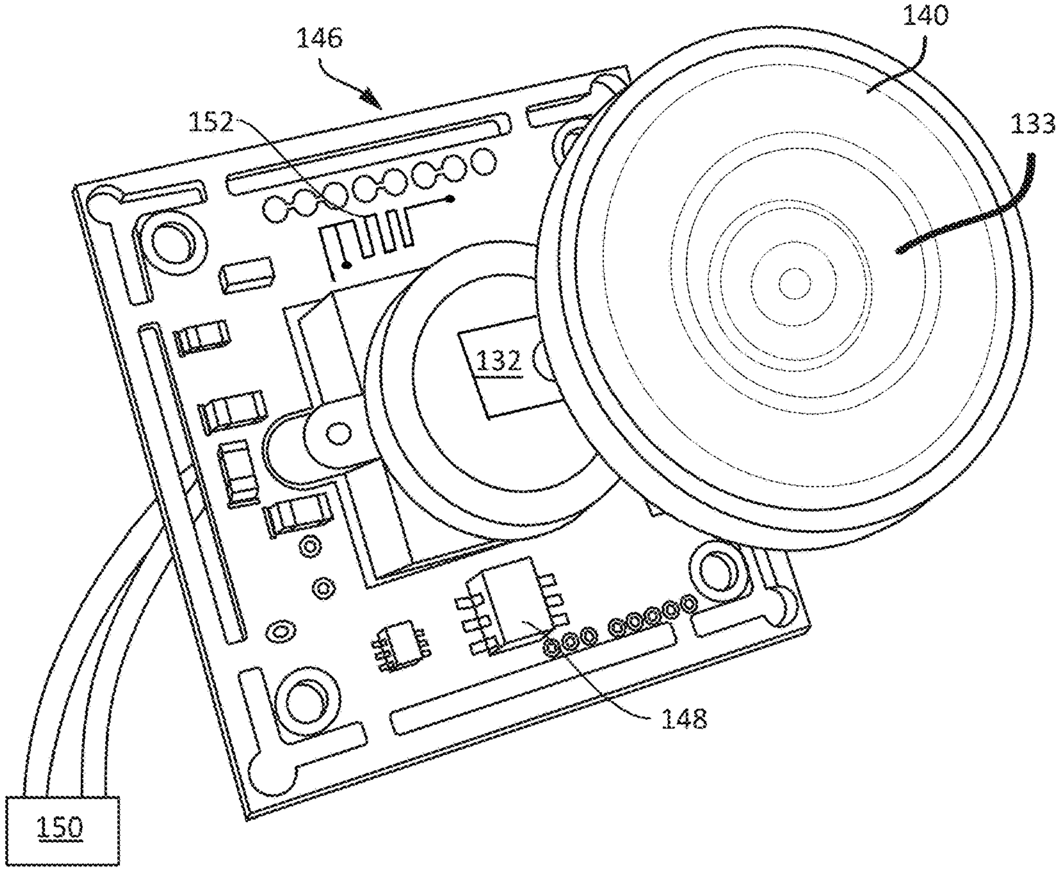
FIG. 3 illustrates a front perspective view of an infrared camera and circuit board that can be used to determine temperature, in accordance with an embodiment of the present disclosure.

FIG. 3 illustrates a front perspective view of a circuit board 146 that includes an optical camera 140 configured as a thermal imaging camera, in accordance with one embodiment. In this example, the optical camera 140 includes a thermal sensor 132 positioned behind a lens 133 and configured to receive light through the lens 133. In some embodiments, the circuit board 146 includes a processor 148 configured to control the thermal sensor 132 and to process acquired raw temperature data. The circuit board 146 can also include a transceiver 152 to communicate temperature information—a temperature value, a thermal image, a captured image, or other information—to the user's computing device 160 or to a processor in a networked computer. In this example, the circuit board 146 is wired to a power supply 150, such as a battery or energized line.

In some embodiments, the temperature sensor 130 includes an integrated field-of-view Passive Infrared Sensor (PIR). For example, the temperature sensor 130 is configured to capture a temperature image within a field of view of the lens 133. Further, in some embodiments, the PIR sensor can be used with the system software to display a frame 166 on the user's computing device 160, where the frame 166 identifies a temperature measurement zone to enable the user to determine whether the visitor is appropriately positioned in the field of view and/or range of the temperature sensor 130.

In one embodiment, the temperature sensor includes a Far Infrared Sensor (FIR) to measure the ambient temperature (e.g., outdoor temperature). The system 250 can determine the ambient temperature in a periodic or continuous fashion. The time period between ambient temperature measurements can be 1 minute, 2 minutes, 5 minutes, 10 minutes, 30 minutes, or some other amount of time. For example, the processor 148 receives ambient temperature measurement data from the FIR sensor of the temperature sensor 130 every 5 minutes. Based on the ambient temperature, the processor 148 can, if needed, compensate for the influence of ambient temperature when determining a visitor's facial skin temperature in order to provide the most accurate body temperature reading. Other acceptable temperature sensors 130 include a far infrared thermal sensor array, a thermal imaging camera, a thermopile sensor, a pyrometer, and a bolometer.

In some embodiments, the system 250 is configured to recognize covered facial areas within the frame 166 and excludes covered areas from being identified as a "hot spot" on the thermal image 164 displayed on the user interface 162. In one example, the processor 148 uses an optical camera 140/141 and processor 148 to detect a face, and based on the temperature values or gradients within that facial region being outside of expected values, the processor 148 can determine whether a visitor has too much of the face covered or has particular regions of the face covered. For example, if the visitor is wearing a facemask, a hat, and/or glasses, or if the visitor's forehead is blocked from view by a face covering or hat, the system 250 can alert the user with a recommendation to ask the visitor to remove the face covering item(s) so that the system 250 can provide an accurate temperature reading.

Figure 4:
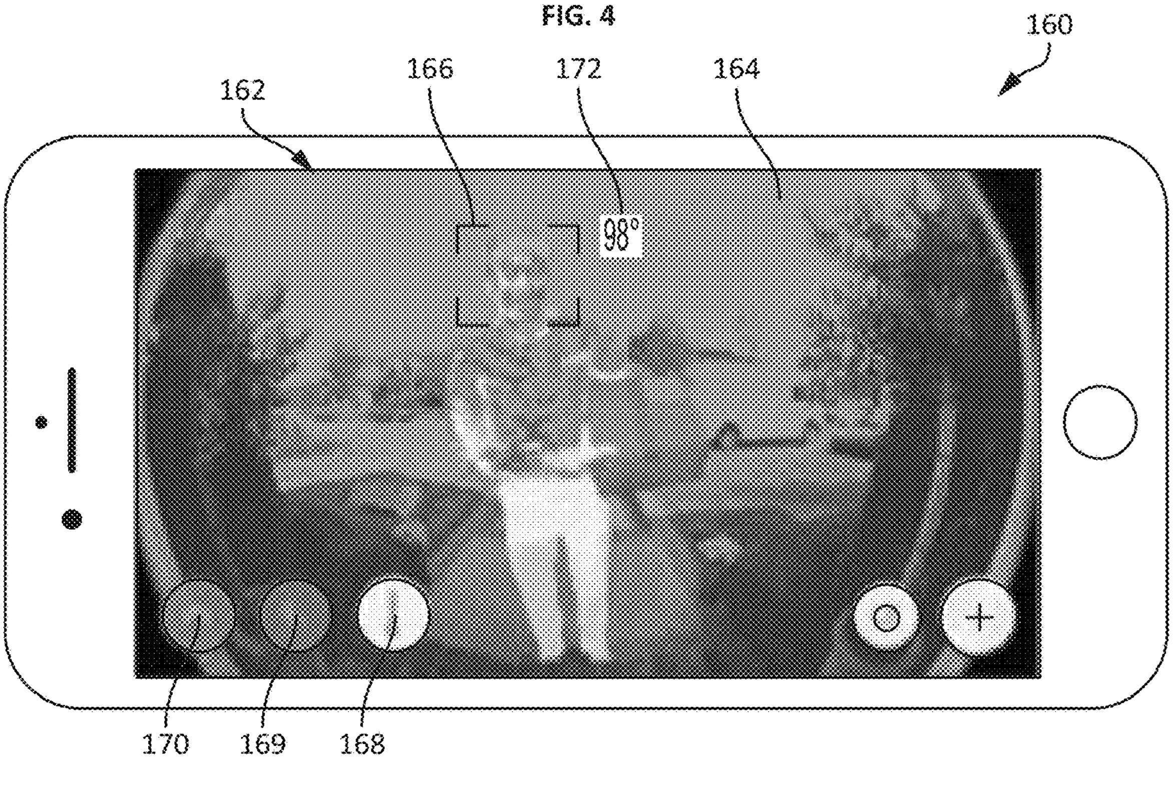
FIG. 4 illustrates a user interface on a computing device (e.g., a cell phone) showing relative temperature within the view and a temperature reading within a selection area, where the view has been communicated wirelessly from the temperature sensor unit to the computing device, in accordance with an embodiment of the present disclosure.

FIG. 4 illustrates a computing device 160 (e.g., a cell phone) with a graphical user interface 162 (e.g., a touch screen) showing a thermal image 164 captured by the temperature sensor 130, in accordance with an embodiment of the present disclosure. The thermal image 164 was received from the sensor unit 120 via a wired or wireless connection to the Internet, a local area network (LAN), a wide area network (WAN), or some other communications network. In this example, the thermal image 164 is displayed with various colors each of which is indicative of a temperature range. In one example, blues and greens represent temperatures up to 75° F., yellow is indicative of temperature from 75-85° F., orange is indicative of temperature from 85-95° F., and red is indicative of temperature from 95-105° F. Other colors can also be used to indicate other temperature ranges, such as temperatures above normal body temperature. In some embodiments, the thermal image 164 is displayed in two tone or monochromatic mode, where a first color or intensity indicates a temperature equal to or above a predefined threshold (e.g., normal body temperature) and a second color or intensity indicates temperatures above the predefined threshold.

The computing device 160 includes software configured to prompt the user and to receive user input via a touch screen, keyboard, mouse, microphone, or some other input method. In one example, the user can use the touch screen of the user interface 162 to select the location and size of a region of interest enclosed by a frame 166, such as by dragging and pinching touch operations. For example, the user may move the frame 166 to any portion of the thermal image 164. After moving the frame 166, or if the computing device 160 does not receive input for a predetermined length of time, the software may automatically accept the frame's location and process (e.g., display) temperature information within the frame 166. Alternately, the computing device 160 can continuously display temperature information of the objects in the frame 166 and update the display when the user moves frame 166.

In some embodiments, the user may first move and/or size the frame 166 as needed, followed by pressing a temperature processing button 168 or the like to initiate collection and processing of temperature information within the frame 166. In this example, the frame 166 includes a view of a visitor's face. Optionally, the user interface 162 includes buttons 169, 170 (or functional equivalent) for determining the high and low temperatures within the thermal image 164 or within the frame 166, depending on how the software is configured. In some embodiments, the user interface 162 displays or otherwise communicates one or more temperatures 172 to the user, whether an average temperature, a minimum temperature, and a maximum temperature, for example.

Figure 5:
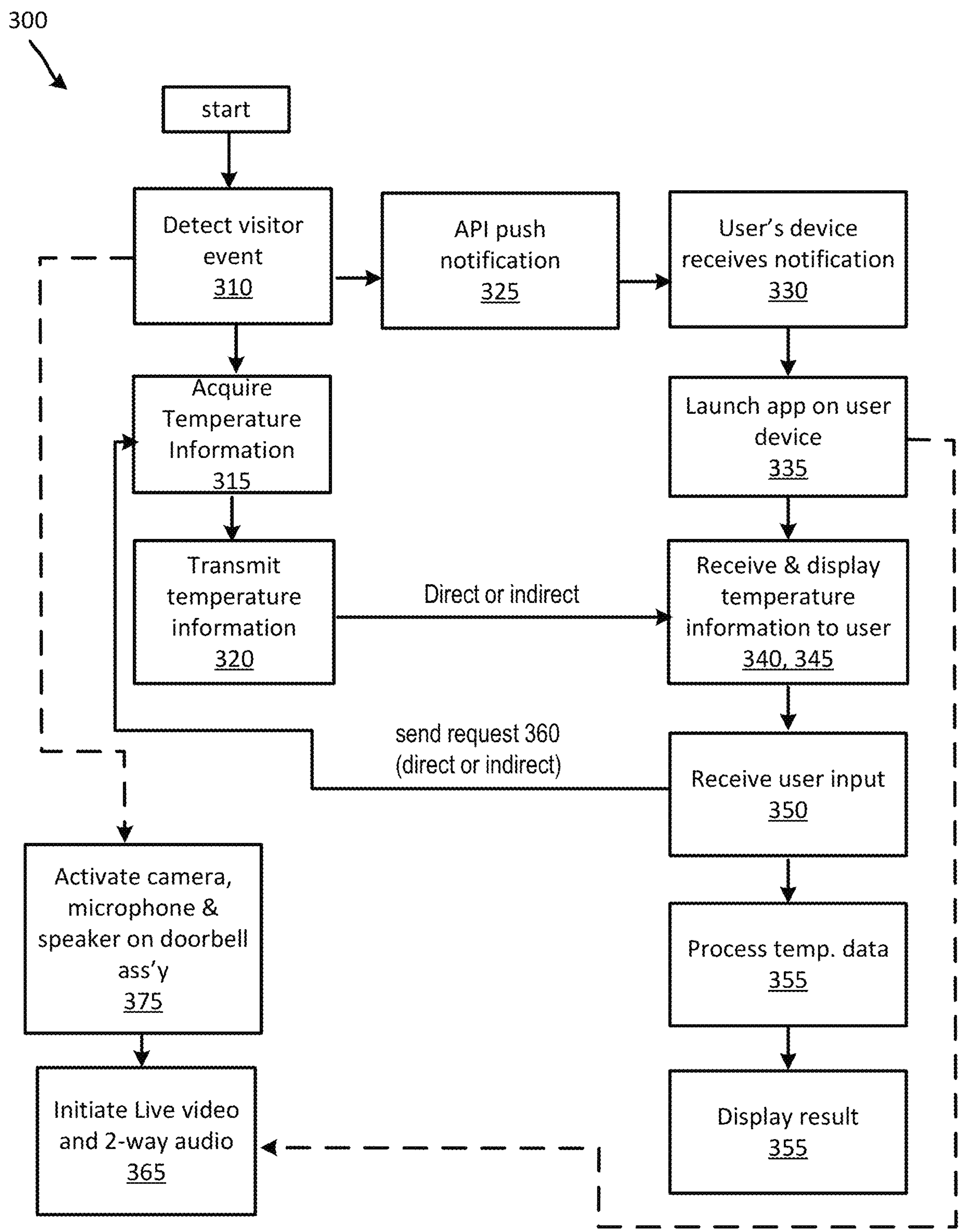
FIG. 5 illustrates a flowchart of processes in a method of detecting a visitor temperature, in accordance with an embodiment of the present disclosure.

FIG. 5 illustrates a flowchart of processes in a method 300 of detecting body temperature of a visitor, in accordance with some embodiments of the present disclosure. Some embodiments of method 300 can be performed with a system 250 that includes a doorbell assembly (e.g., a video doorbell), a sensor unit 120 with temperature sensor 130, an application programming interface (API), and a software application on the user's computing device 160, such as a personal computer, a laptop computer, a tablet computer, or a mobile phone. Other configurations of system 250 can be used as will be apparent in light of the present disclosure.

In one example, the doorbell assembly 110 is a video doorbell assembly that includes a video camera, a doorbell button, a microphone, and a speaker. The system 250 also includes a sensor unit 120 with a temperature sensor 130, such as an IR thermal imaging sensor. The sensor unit 120 can be integral to the doorbell assembly 110 or can be a distinct unit. In one example, the doorbell assembly 110 produces an audible chime when a visitor presses the doorbell button. In addition, or in the alternative, pressing the doorbell button may result in a signal to the processor. For example, pressing the doorbell button causes the system to open communications software on the user's computing device to enable communication via the video camera, speaker, and/or microphone. The video doorbell assembly also includes communications hardware needed to communicate with the user via wireless communications.

In some embodiments, the temperature sensor 130 includes a thermal imaging camera. In other embodiments, the thermal imaging hardware and software are part of a sensor unit 120 that is distinct from the doorbell assembly 110 and that communicates directly or indirectly with the doorbell assembly 110 via wired or wireless means, where such communication can use the doorbell assembly's communications hardware or can use its own communications hardware. In one embodiment, the sensor unit 120 is separate from the doorbell assembly and operates independently from the doorbell assembly. In one such embodiment, the sensor unit 120 is configured to detect the audible chime of the doorbell assembly 110. Alternately, the sensor unit 120 can include a motion sensor or audio sensor that is part of the sensor unit 120, for example.

Method 300 begins with detecting 310 a visitor event. For example, the visitor event is the presence of a visitor to an entry door of a residence or other access point. Detecting 310 the visitor event can be performed by a doorbell assembly and/or a sensor unit, depending on the system configuration. Detecting the visitor event can be performed using a motion sensor, a proximity sensor, a microphone (e.g., to detect sound), the doorbell assembly receiving user input (e.g., a doorbell button touch), a change in a thermal data captured by thermal imaging camera, or some other means of the doorbell assembly or temperature sensor unit detecting a visitor to the door.

In one example, detecting 310 the visitor event includes detecting an audible doorbell chime or knocking on the door. In one such embodiment, a microphone and signal processor of the sensor unit can be used to detect an audible doorbell chime or knocking, where the signal processor "looks" for an audio signal having certain characteristics, such as minimum signal strength and a particular audio wave shape consistent with a chime or knocking.

Upon detecting 310 a visitor event, method 300 continues with turning on the sensor unit (if not already on) and acquiring 315 temperature information. Acquiring 315 temperature information can be performed with a temperature sensor, such as an infrared camera or other thermal imaging device. The temperature data typically includes a skin temperature of the visitor's facial region, such as the forehead or tear duct. However, the temperature information is not limited to skin temperature and can additionally or alternately include any one or more of an ambient temperature, a point temperature, light energy at one or more wavelengths, an emissivity value, a thermal image, a thermal video, a temperature gradient, a high temperature, a low temperature, and a reference temperature.

Method 300 continues with sending 320 the temperature information to the user's computing device. In some embodiments, sending 320 the temperature information utilizes an application programming interface (API) or hub to relay the information. When the configuration permits, temperature information can be sent directly to the user's computing device via a Bluetooth radio or Wi-Fi radio. In some embodiments, system 250 utilizes the sensor unit, a server computer, the user's computing device, or a combination of devices to convert temperature information acquired by the sensor unit to a body temperature value to be displayed to the user.

Detecting 310 a visitor event also results in the sensor unit pushing 325 a notification to the user's computing device via an API. When the user's computing device receives 330 the notification from the API and/or the user acknowledges the notification, the computing device launches 335 the software application that includes a user interface (if not already running). With the software application operating, the user's computing device receives 340 the temperature information acquired by the sensor unit and, after any needed processing, the computing device displays 345 the temperature information to the user via the user interface. The displayed temperature information can include one or more of a temperature map, one or more temperature values, and a status notification (e.g., a warning of high body temperature or an indication of normal temperature), for example.

Optionally, the user's computing device receives 350 user input, such as a button press or touch-screen selection. In one example, the user input can include selecting a region of interest by touching the screen, touching the screen to drag a selection box to a desired region of the display, sizing a selection field using a two-finger "pinch" technique, selecting from a list of options, speaking a selection, entering a selection using a keyboard or mouse, or other input to the computing device. In response to the received user input, the computing device processes 355 data received in step 340 and displays 355 the result to the user. Optionally, additional temperature data can be acquired by the user's computing device sending 360 a request to the sensor unit (e.g., via the API) to request additional temperature data. Such additional data can be communicated to the user's computing device and displayed to the user as discussed above with processes 315, 320, 340, and 345.

In some embodiments, method 300 includes initiating 365 live video and/or 2-way audio communication with the visitor via the doorbell assembly (e.g., a video doorbell assembly) or other system component. In some embodiments, initiating 365 communication includes relaying information directly or via a network hub or API to activate 375 an optical camera and microphone. In other embodiments, the doorbell assembly activates 375 the microphone and speaker as a result of detecting 310 the visitor event.

Figure 6A:
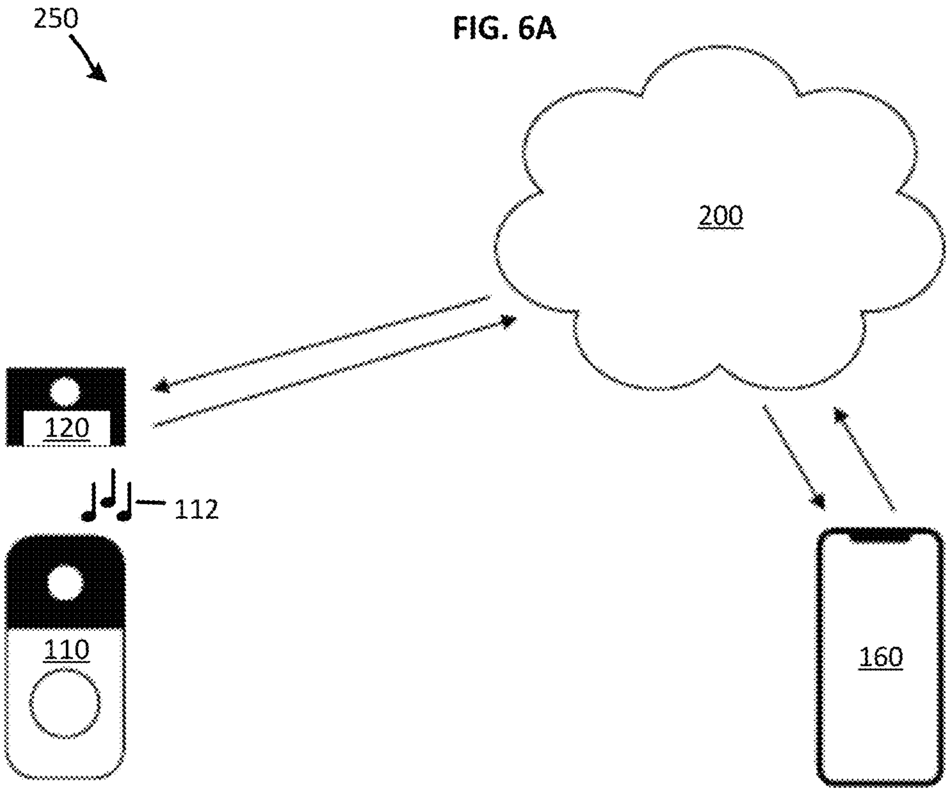
FIG. 6A illustrates a diagram showing components of a doorbell system that includes a temperature sensor unit, a doorbell, and a computing device, in accordance with one embodiment.
Figure 6B:
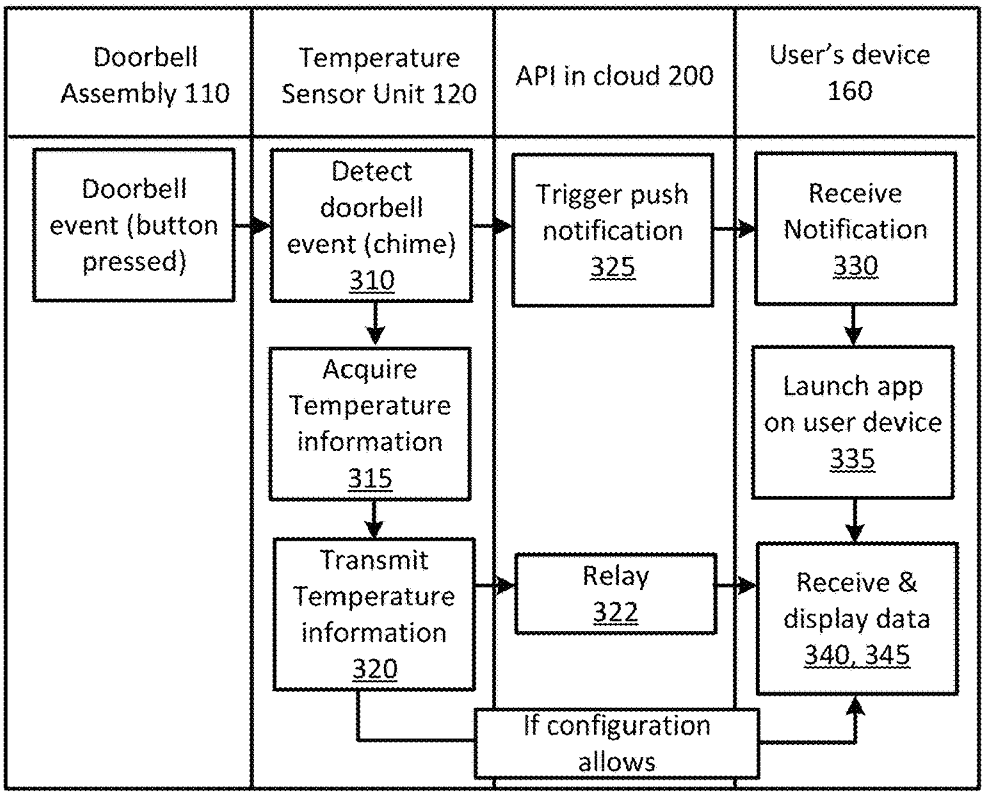
FIG. 6B is a diagram showing resource allocation for processes in a method of detecting visitor temperature using the system of FIG. 6A, in accordance with an embodiment of the present disclosure.

FIG. 6A illustrates a diagram showing components of a system 250 useful for performing method 300 discussed above, in accordance with one embodiment. FIG. 6B is a diagram showing processes of method 300 allocated to a particular component of the system 250. In FIG. 6B, processes are arranged in columns with the component listed in the cell above each column. Note that this particular allocation of processes and components shown in FIG. 6B is not required in all cases and some processes can be performed by a different component, depending on the particular arrangement and configuration of system components. In this example, the system 250 includes a doorbell assembly 110, a sensor unit 120, and system software configured with an application programming interface (API) 200 in the "cloud" and a software application ("app") on the user's computing device 160. The sensor unit 120 is configured to detect an audible chime 112 from the doorbell assembly 110. Upon detecting 310 the chime 112 (or other visitor event), the sensor unit 120 communicates with the user's computing device 160 via software and API 200. One advantage of a system as illustrated in FIG. 6A is that the sensor unit 120 can be a separate component that is used with an existing doorbell assembly 110 and operates independently of the doorbell assembly 110. Accordingly, in some embodiments, the doorbell assembly 110 can be considered optional, such as when the sensor unit 120 includes a motion sensor or other device to detect a visitor (a "doorbell event"), or when the sensor unit 120 detects the audible chime of a traditional doorbell or a knocking sound.

Figure 7A:
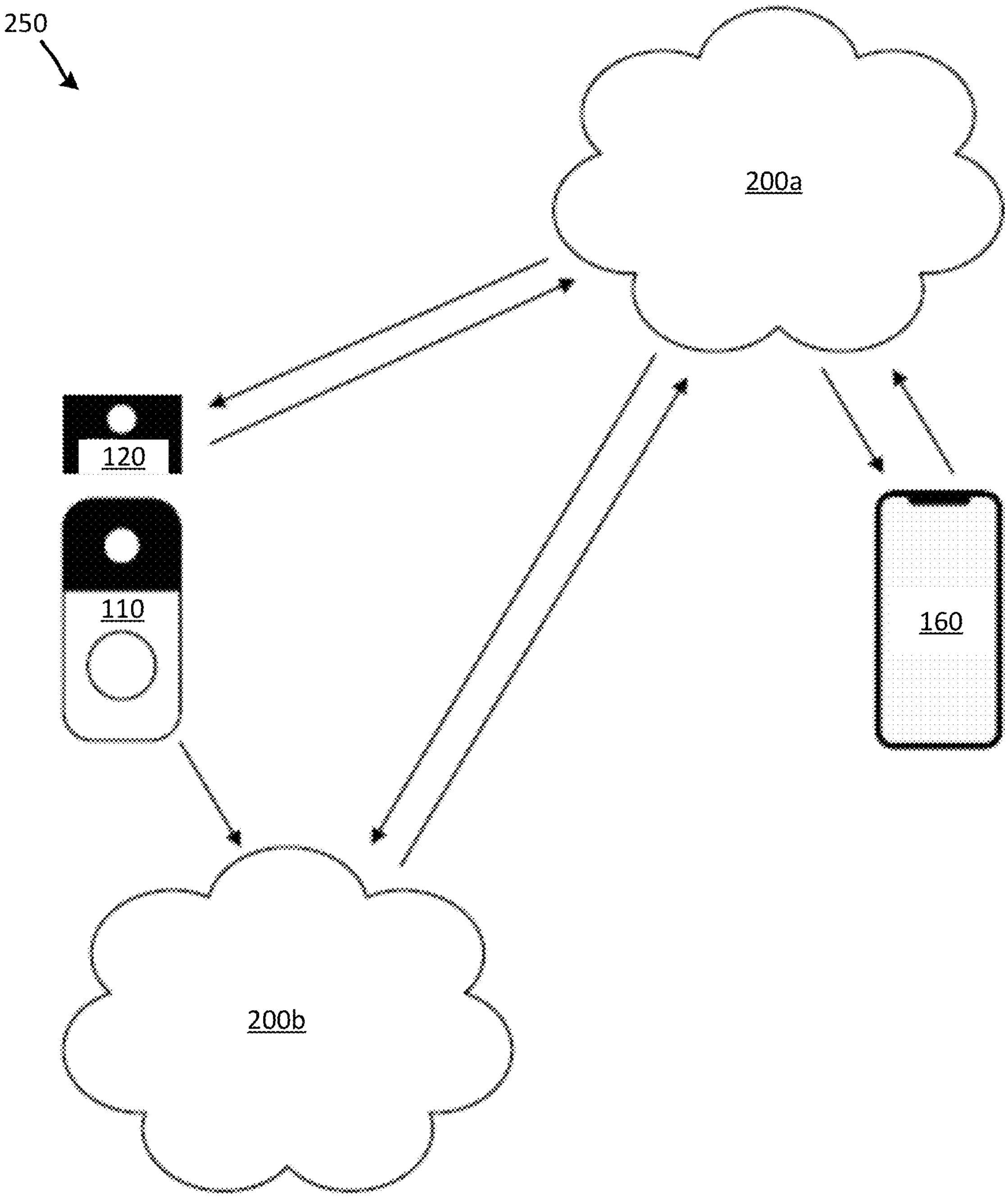
FIG. 7A illustrates a diagram showing components of a system configured to detect the temperature of a visitor, in accordance with another embodiment.
Figure 7B:
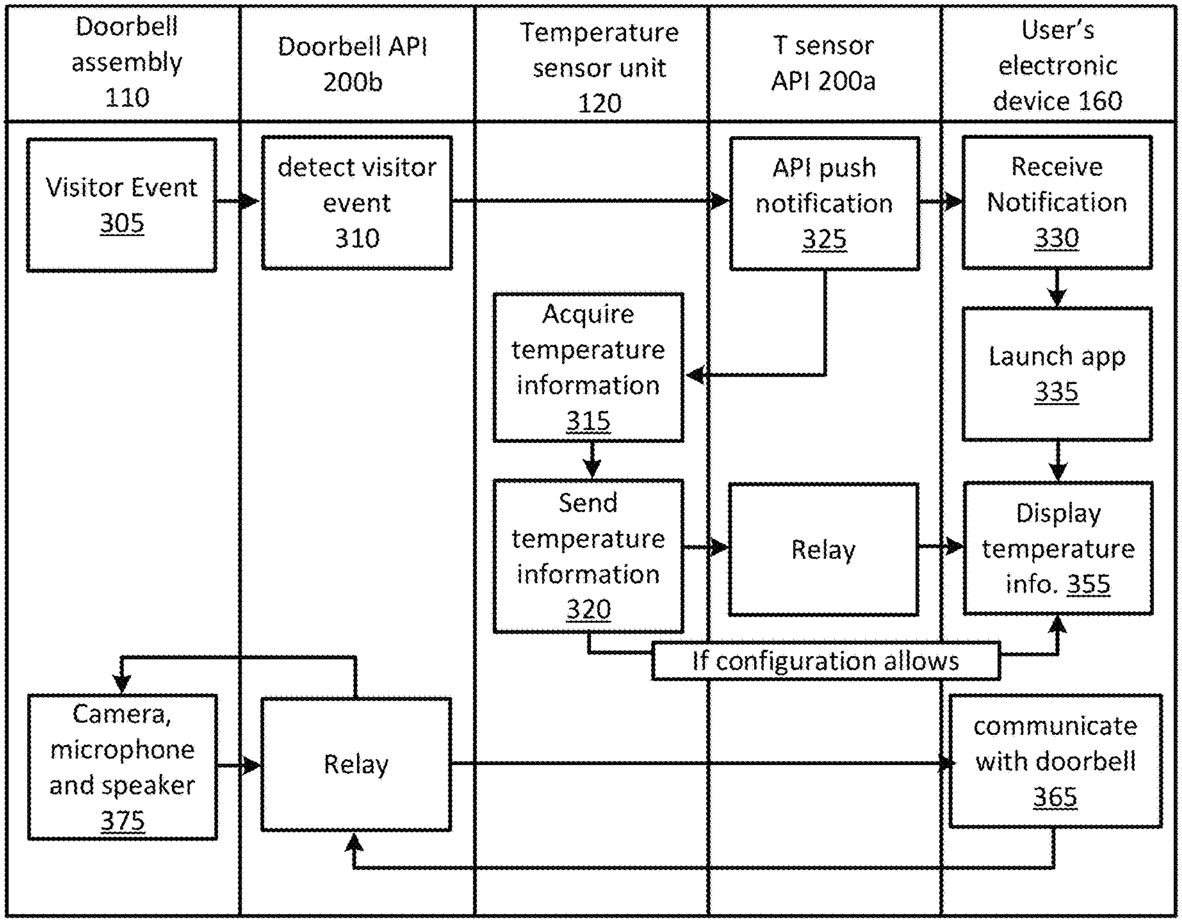
FIG. 7B is a diagram showing resource allocation for processes in a method of detecting visitor temperature using the system of FIG. 7A, in accordance with an embodiment of the present disclosure.

FIG. 7A illustrates a diagram showing components of a system 250 that can be used to perform method 300 discussed above, in accordance with another embodiment. FIG. 7B is a diagram showing processes of method 300 allocated to a particular component of the system 250 by column arrangement with the component listed in the cell above each column. In this example, the system 250 includes a doorbell assembly 110, a sensor unit 120, and system software configured with a sensor unit application programming interface (API) 200*a* in the cloud, system software with a doorbell application programming interface (API) 200*b* in the cloud, and a software application ("app") on the user's computing device 160. The sensor unit 120 is configured to communicate directly or indirectly with the doorbell assembly 110, such as a wired connection or via a wireless connection via Bluetooth, Wi-Fi, or other radio frequency communications protocol. The sensor unit 120 communicates wirelessly with the user's computing device 160 via software and sensor unit API 200*a*. The doorbell assembly 110 communicates with the computing device 160 using the doorbell API 200*b*. Using the doorbell API 200*b* and/or the sensor unit API 200*a*, the sensor unit 120, doorbell assembly 110, and user's computing device 160 communicate. Note that this particular allocation of processes and components is not required in all cases and some processes can be performed by a different component, depending on the particular arrangement and configuration of system components.

In the system 250 depicted in FIGS. 7A-7B, the temperature sensor unit API 200*a* can be an "unofficial" API that works with the doorbell API 200*b*, or an API that is certified to work with the doorbell API 200*b*. In embodiments where the sensor unit API 200*a* is certified to work with the doorbell API 200*b*, doorbell software on the user's computing device 160 can be upgraded or modified to communicate with the sensor unit 120, capture temperature data, and display temperature information, for example. For example, the doorbell software is modified to include a user interface with a temperature display and user input to control the sensor unit 120. In other embodiments, the sensor unit 120 can be integral to the doorbell assembly 110 or can be a hardware add-on that is designed to operate with the doorbell assembly 110.

Figure 8A:
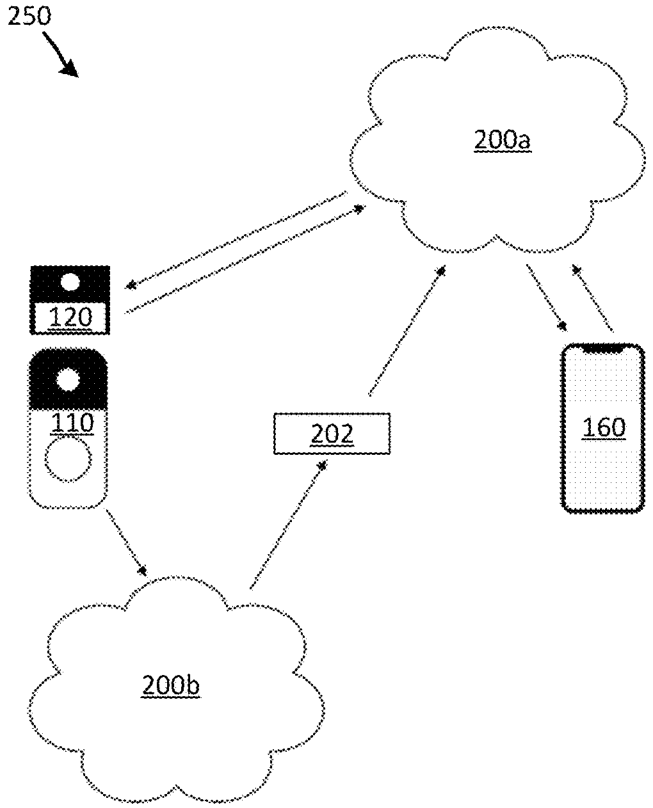
FIG. 8A illustrates a diagram showing components of a system configured to detect temperature of a visitor, in accordance with yet another embodiment.
Figure 8B:
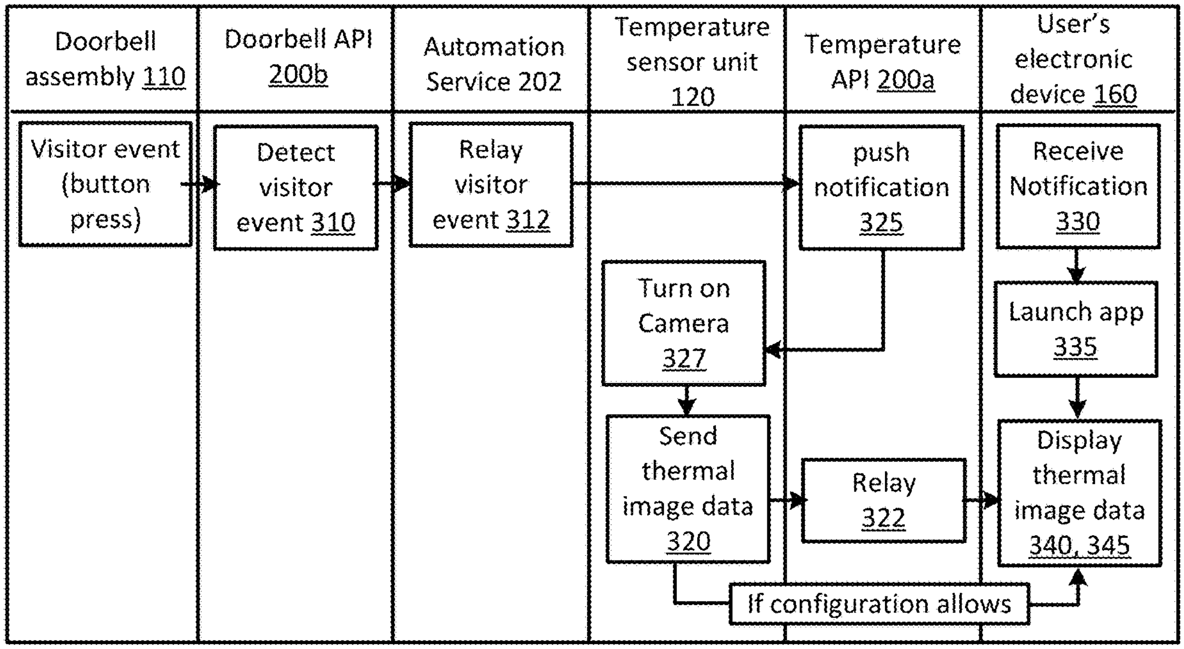
FIG. 8B is a diagram showing resource allocation for processes in a method of detecting temperature of a visitor and using the system of FIG. 8A, in accordance with an embodiment of the present disclosure.

FIG. 8A illustrates a diagram showing components of a system 250 that can be used to perform method 300 discussed above, in accordance with yet another embodiment. FIG. 8B is a diagram showing processes of method 300 allocated to a particular component of the system 250 as indicated by aligning the process(es) in a column with the component listed in the cell above each column. In this example, the system 250 includes a doorbell assembly 110, a sensor unit 120, system software configured with a sensor unit application programming interface (API) 200*a* in the cloud, system software with a doorbell application programming interface (API) 200*b* in the cloud, a software application ("app") on the user's computing device 160, and automation software 202. In some embodiments, the automation software 202 enables a user to program a response to events, such as communication between components in system 250 or a response to user input. One such automation software 202 is sold by If This Then That, Inc.

Figure 9:
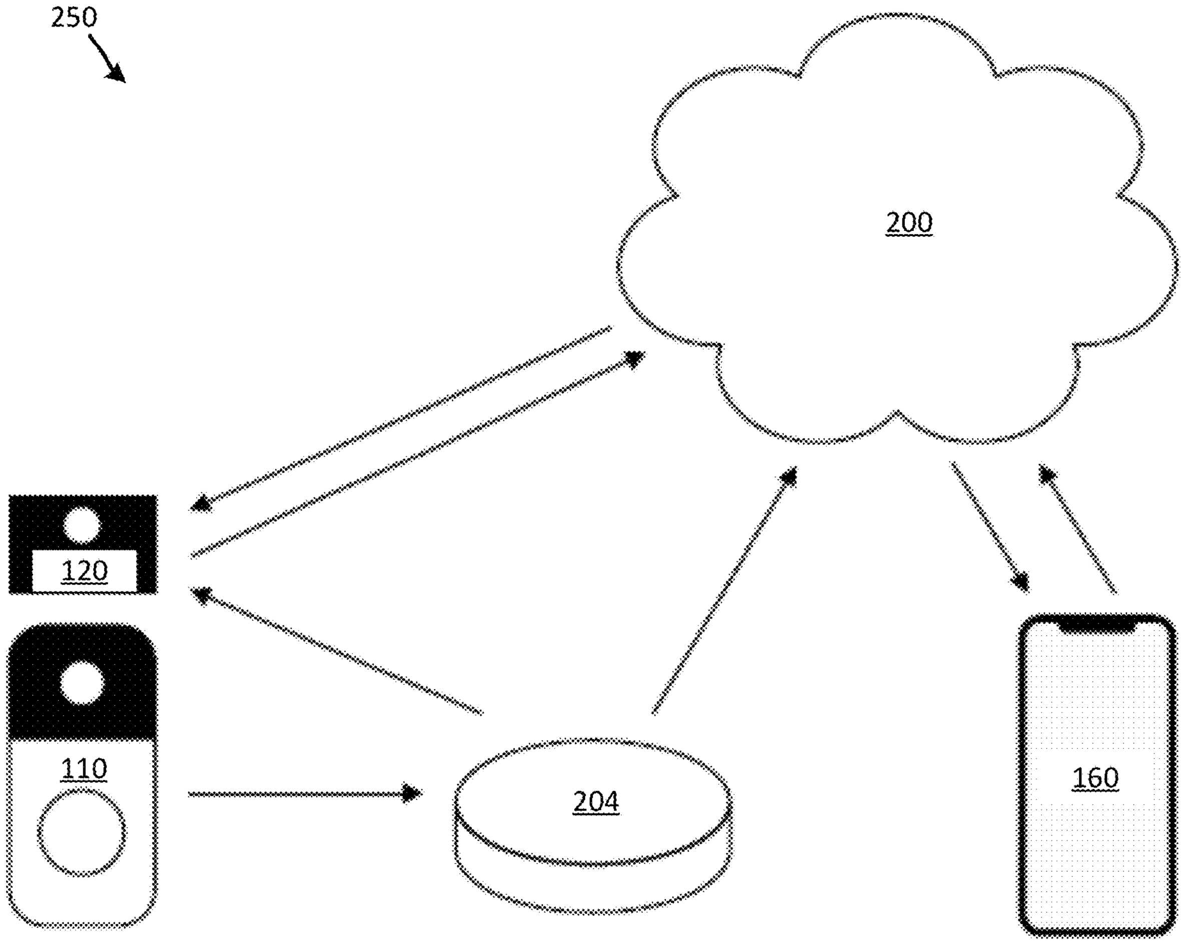
FIG. 9 illustrates a diagram of a system that includes a communications hub, in accordance with another embodiment.

FIG. 9 illustrates system 250, in accordance with another embodiment. In this example, system 250 includes a network device 204 providing network communications functionality. In some embodiments, the network device 204 uses a wireless communications protocol and is configured for home automation. One such network device 204 is known as a Z-Wave Hub and utilizes a mesh network with low-energy radio waves to communicate from device to device. Such network device 204 enables wireless control of the doorbell assembly 110 and/or the sensor unit 120. For example, the network device 204 functions as a hub connected to the doorbell assembly 110, the sensor unit 120, and sensor unit API 202*a*. The network device 204 provides multiple paths for communication from the doorbell assembly 110 to the user's computing device 160, namely, through the sensor unit 120 and sensor unit API 202*a*, or directly via the sensor unit API 202*a*.

The sensor unit 120 is configured to communicate with the doorbell assembly 110 using a wired connection or via a wireless connection, such as Bluetooth communication, Wi-Fi communication, or other radio frequency communications protocol. The network hub 204 receives communications from the doorbell assembly 110 and forwards those communications to an API 200 or to the sensor unit 120. Accordingly, the doorbell assembly 110 can communicate with the computing device 160 via the network device and API 200. The sensor unit 120 communicates with the user's computing device 160 via the API 200. Although some arrows in FIG. 9 indicate that communication may be one-directional, this is not required. In some embodiments, for example, the network hub 204 communicates data from the sensor unit 120 to the doorbell assembly 110, such as to enable communication with the visitor via the doorbell assembly 110 in embodiments where the sensor unit 120 operates independently of the doorbell assembly 110.

Figure 10A:
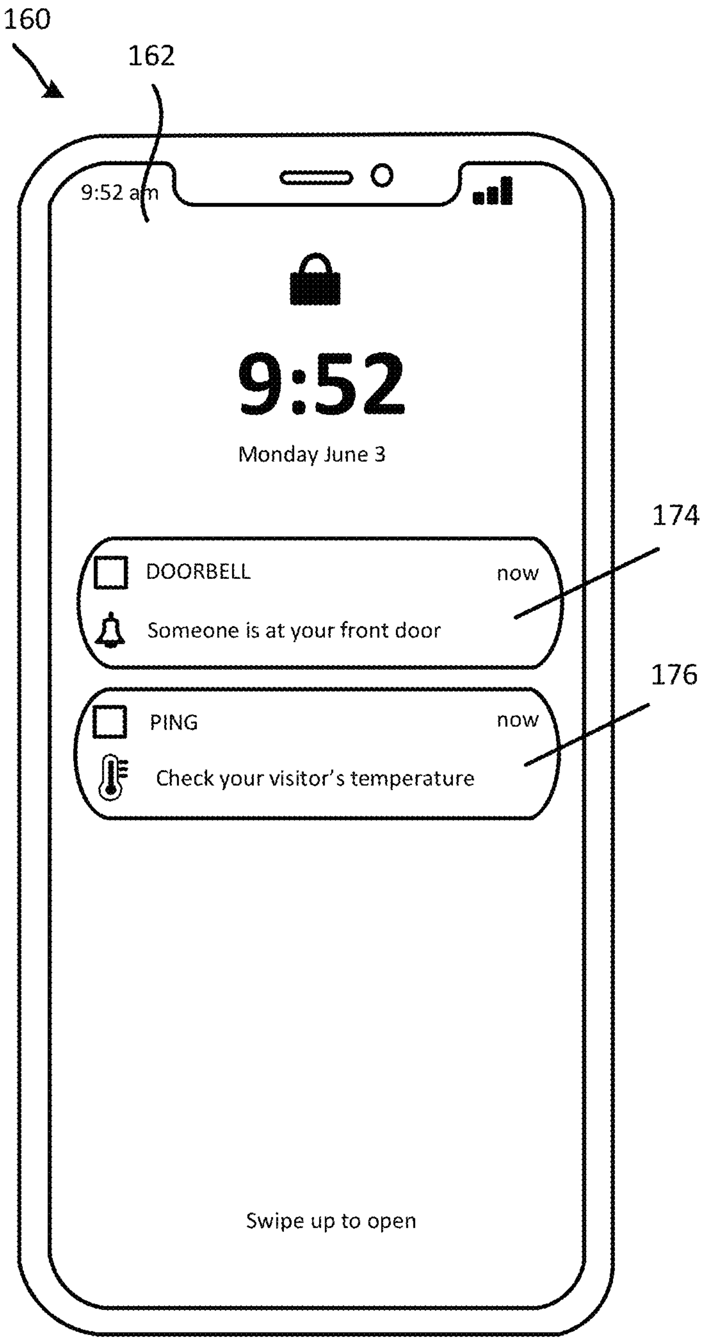
FIGS. 10A-10E illustrate examples of a user interface on a user's computing device, in accordance with some embodiments.

Referring now to FIGS. 10A-10E, a user interface 162 on the user's computing device 160 is illustrated at various stages of method 300, in accordance with some embodiments. In FIG. 10A, the computing device 160 displays an alert 174 indicating to the user that a visitor is at the door. Below the alert 174 is a prompt 176 to check the visitor's temperature. When the user presses the prompt 176, the system activates temperature sensing to determine a body temperature of the visitor.

Figure 10B:
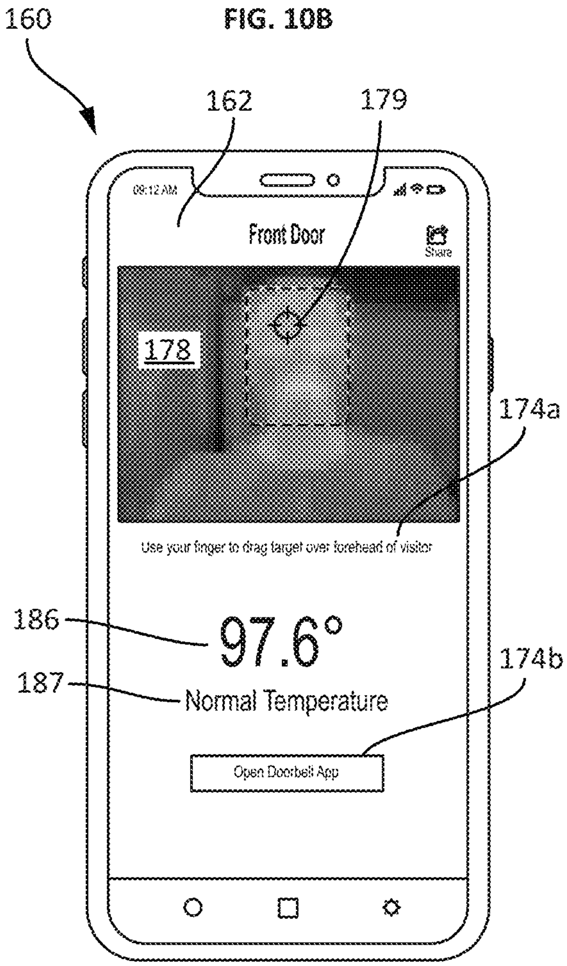
Figure 10C:
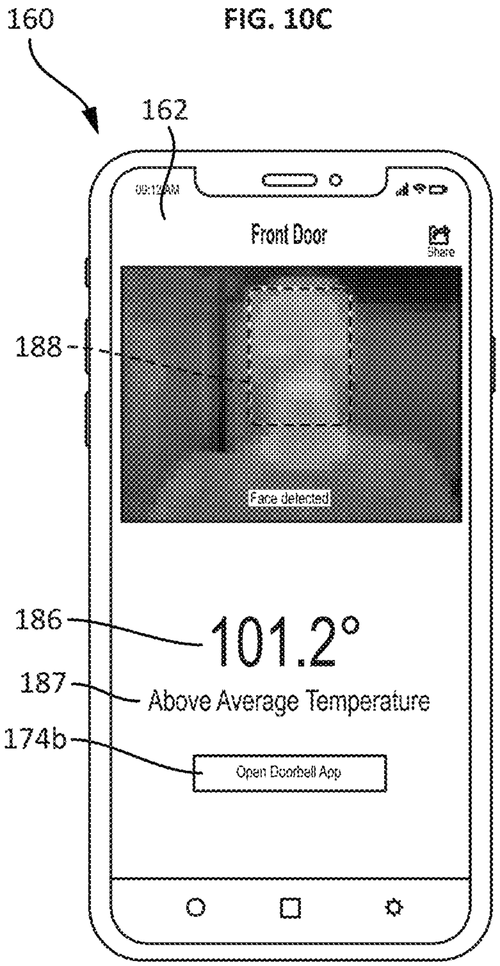

FIGS. 10B and 10C show an example of the user interface 162 in an embodiment where the sensor unit 120 does not communicate with the doorbell assembly 110. For example, access to an API is not available and the user must open the doorbell software application to enable communication with the visitor. In this example, the user interface 162 displays a color-coded temperature map 178, using software of the sensor unit 120, to display temperature data acquired by the sensor unit 120. The user interface 162 provides the option for the user to open the doorbell software application to initiate communication with the visitor using the doorbell assembly's 110 optical camera 140 and microphone 134.

In each of these examples, the user interface 162 displays a temperature map 178, a position selector 179 or selection box 188, and a display of the temperature 186. In the example of FIG. 10B, the displayed temperature 186 corresponds to the location where the position selector 179 is located. The user interface 162 also displays a first prompt 174*a* informing the user to use a finger to drag the position selector 179 to the desired area (e.g., forehead of the visitor). In FIG. 10C, the displayed temperature 186 is a high temperature within the selection box 188. Although shown displayed in these examples, the temperature 186 value is not displayed in all embodiments.

Each user interface 162 optionally displays a notice 187 indicating the status of the temperature at the position selector 179 or within the selection box 188, such as being consistent with normal body temperature or above normal body temperature. A second prompt 174*b* is a button that, when touched, will open the doorbell software to enable communication via the doorbell's video camera and/or microphone. In FIG. 10C, the temperature 186 reads 101.2°; accordingly, the notice 187 states that this in an abnormal body temperature. The user interface 162 in FIG. 10C also displays a selection box 188 indicating that a face has been detected.

Figure 10D:
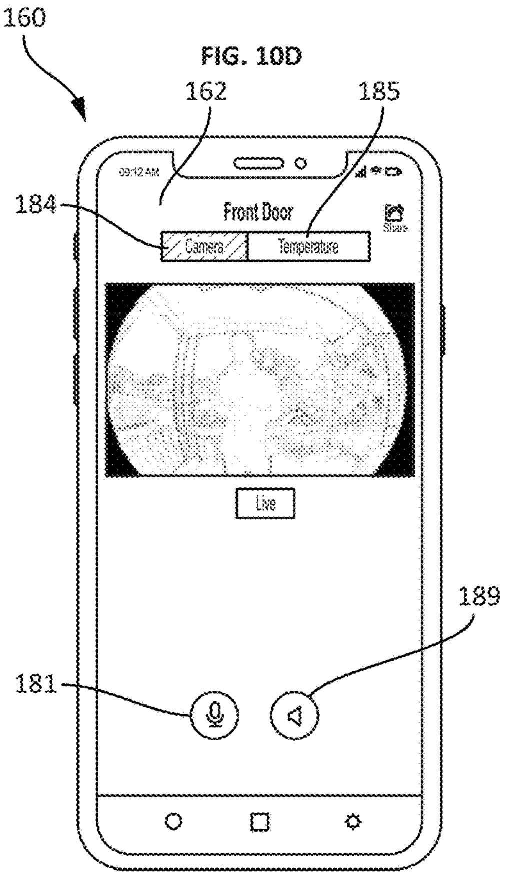
Figure 10E:
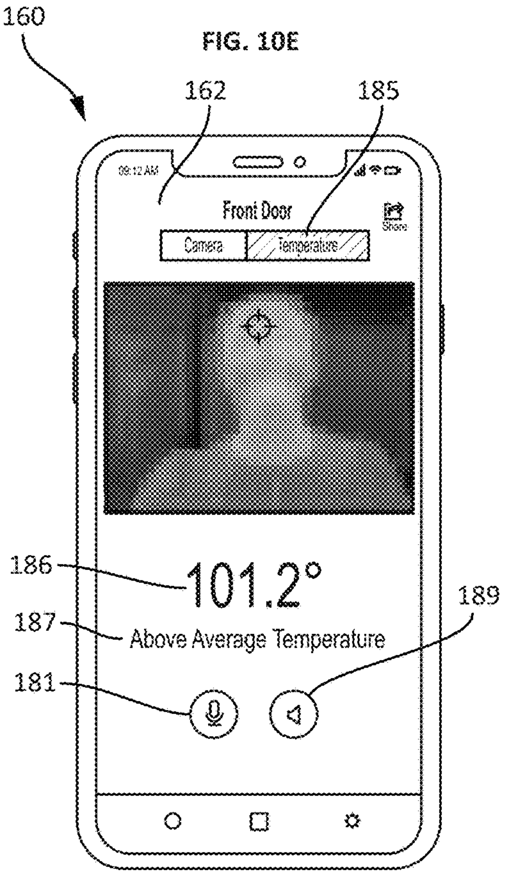

The user interfaces of FIGS. 10D and 10E are examples of an embodiment in which API access is used to combine audio and video of the doorbell assembly 110 with temperature acquisition and display of the sensor unit 120. In FIG. 10D, the user interface 162 displays the video capture from the doorbell assembly's optical camera. This user interface 162 can also display temperature information acquired by the sensor unit 120 when the user presses the temperature icon 185. The user interface 162 of FIG. 10D also displays a camera icon 184 (shown active), a microphone icon 181, and a speaker icon 189. In this example, the camera icon 184 is illuminated as being active. Pressing the temperature icon 185 would switch the user interface 162 to display the temperature map, such as shown in FIG. 10E. The user can turn on or off the microphone by pressing the microphone icon 181 and turn on/off the phone's speaker by pressing the speaker icon 189. In FIG. 10E, the user has selected the temperature icon 185 on the user interface 162, which is now highlighted to indicate the temperature mode is active. The user interface 162 displays the temperature 186, notice 187, microphone icon 181, and speaker icon 189.

In use, embodiments of system 250 can be used to detect and communicate temperature information of a visitor to the user's computing device 160. The system 250 can be configured so that the sensor unit 120 is adapted to acquire temperature data, and to communicates with the doorbell assembly 110. Alternately the system 250 can be configured so that the sensor unit 120 operates independently of the doorbell assembly 110. For example, the sensor unit 120 is disposed in proximity with the doorbell assembly 110, such as within communication range using a Bluetooth communications protocol, with a range of 20 feet, with a range of 15 feet, within a range of 10 feet, within a range of 5 feet, or within a range of 1 foot. Numerous variations and embodiments will be apparent in light of the present disclosure.

Figure 11:
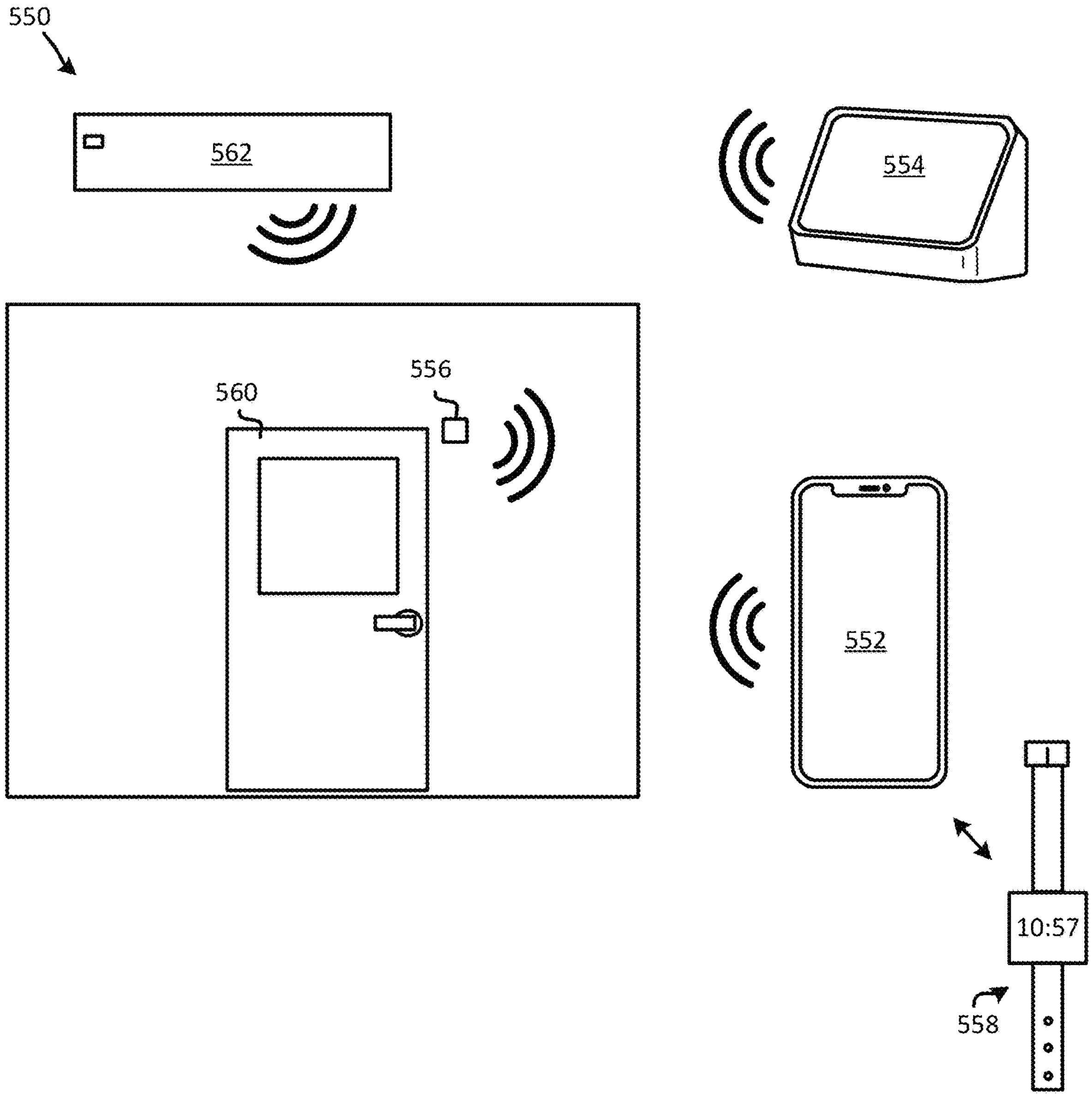
FIG. 11 illustrates an example system for sharing health information between devices, in accordance with an embodiment of the present disclosure.

Referring now to FIG. 11, a system 550 is configured for sharing health information, in accordance with an embodiment of the present disclosure. In one embodiment, system 550 includes a first computing device 552, a second computing device 554, a sensor 556 positioned adjacent (or configured to be positioned adjacent) an entry 560, and a third computing device 562, such as a networked computer or cloud-based server computer. Optionally, the system 552 includes one or more wearable devices 358 disposed in communication with the first computing device 552. In some embodiments, the system 550 can be a smart home network, where the third computing device 562 is a network hub or networked computer of the smart home system. For example, the third computing device 562 can be a smart display, a personal computer, a tablet, or a network hub or a smart home network, or it can be a cloud-based computer in communication with other components of the smart home network via Wi-Fi.

The first computing device 552 and second computing device 554 can be any suitable electronic device, include a mobile phone, a personal computer, a laptop computer, a tablet computer, a smart speaker, a television, or other suitable electronic device equipped with wireless communication technology and capable of operating system software. In the example shown in FIG. 11, the first computing device 552 is a portable electronic device, such as a smart phone or tablet computer, and the second computing device 554 is a smart display, such as a component of a smart home network. In another example, the first and second computing devices 552, 554 are smart phones with installed software, where the smart phone has the ability to communicate via one or more of Wi-Fi, cell service, Bluetooth (e.g., Bluetooth Low Energy radio (BLE)), RF communication, or other communications protocols. The software on the first and second computing devices 552, 554 is configured to send and receive data, display notifications to the user, and communicate with other system devices. The system software also runs on the third computing device 562, such as a cloud-based server, or a home computer or network hub to enable or facilitate communication among system devices and perform computations as needed.

In one embodiment, the first computing device 552 contains stored health information of the user, who may be referred to as a first user or visitor. In one embodiment, the stored health information includes one or more of vaccination status and/or history, blood type, age, medication information, health history, health condition(s), body temperature, pulse rate, and blood pressure. Some health information can be acquired from a wearable device 558 on the first user's person. For example, the first computing device 552 acquires temperature data, pulse rate, or other health information from a smart watch or other suitable wearable device 558 using a Bluetooth communication between the wearable device 558 and the first computing device 552.

The first user can use the first computing device 552 to store a vaccination record for COVID-19 or other illness. The stored health information can be in any suitable electronic format, including a 2D barcode (e.g., a QR code), encrypted data, image, text, or combination thereof. The first user additionally or alternately can share health information that is communicated to the first computing device from a wearable device 558. For example, system software obtains body temperature and pulse rate from the wearable device 558 at the time the first computing device shares health information. The first user additionally or alternately can authorize the system 550 to acquire health information from a database accessible using an Internet connection. For example, the first user authorizes the system 550 to access vaccination history from a medical database by sending or otherwise providing log-in information to the system. The information can be encrypted to protect privacy. In embodiments where an optical camera is present, the optical camera can acquire an image of a 2D barcode displayed on the first computing device 552, which when processed, links the system to a vaccination or health data record located on the visitor's computing device (e.g., a Smart Phone) or stored on a remote database. For example, the remote database is a health insurance portal, a medical practitioner portal, an employer human resources portal, or other database where the first user can authorize the system to access to the database to retrieve certain health information.

The third computing device 562 can be a network computer or equivalent device disposed in communication with the sensor 556 and with the second computing device 554 using wired or wireless means. The third computing device 562 can be a server computer (e.g., a "cloud computer" or home computer), a desktop computer, a laptop computer, a tablet computer, a network hub, a smart display, or a mobile phone, to name a few examples. In one example, the third computing device 562 is a cloud computer or server that communicates with the sensor 556 and with the second computing device 554 using an application programming interface (API) and by sending push notifications to devices running the system software. In another example, the third computing device 562 communicates with the first and second computing devices 552, 554, but may or may not communicate with the sensor 556. For example, when the sensor 556 detects the first computing device 552, the system software causes the first computing device 552 to communicate health information and/or messaging to the second computing device 554 via the third computing device 562 (e.g., a cloud-based server computer).

The sensor 556 is located near the entrance 560 of a building, home, business, or other structure visited by the user of the first computing device 552 and occupied by (or controlled by) the user of the second computing device 554. The sensor 556 can communicate with system devices using RF communication, Wi-Fi radio, and/or Bluetooth Low-Energy radio (BLE), for example. The sensor 556 alternately or additionally can have a wired connection to the second and/or third computing devices 554, 562. The sensor 556 can be part of a sensor assembly that includes a RF transceiver, an optical camera, a motion sensor, a speaker, a microphone, and one or more buttons. In one embodiment, the sensor 556 is part of a video doorbell assembly, such as discussed above. In other embodiments, the sensor 556 can be a stand-alone sensor assembly configured to communicate wirelessly with the first computing device 552 as it approaches the entry 560. For example, the sensor 556 detects the presence of the first computing device 552 using RF pinging. In another example, the sensor 556 operates using passive RF communication and turns on when it receives a beacon signal broadcast by the first computing device 552. For instance, when the first computing device 552 is within range, the sensor 556 receives the ping and responds by transmitting a reply signal to the first computing device 552. Upon receiving the reply, the first computing device 552 initiates communication with the third computing device 562 (e.g., cloud server). Alternately, the sensor 556 initiates communication with the third computing device 562 after detecting the first computing device 552.

The wearable device 558 can be a watch, fitness tracker, a microchip embedded in clothing or clothing accessory of the visitor, a microchip implanted in the body of the visitor, or other wearable electronic device in wireless communication with the first computing device 552. For example, the wearable device 558 is a smart watch worn by the user of the first computing device 552, where the smart watch is configured to detect skin temperature and pulse rate, and communicates wirelessly with the first computing device 552, such as by using Bluetooth communication. The wearable device 558 can be configured to detect and report current health information of the user, such as pulse rate, skin temperature, body temperature, and blood pressure. In some embodiments, the wearable device 558 detects body temperature of the user and serves as a temperature sensor 130 in some embodiments. The wearable device 558 can further be configured to store one or more records of health information collected over a period of time. For example, the stored information can be or include a record of data collected over the course of an hour, day, week, month, or other time frame.

In one embodiment, the system software enables the first user to collect and/or store health information as well as to selectively communicate some or all of that health information to another device running the system software. The system software also enables the system to access health information stored on a remote computer via an Internet connection, such as a health insurance portal, in some embodiments. The system software further enables the first user to add personal contacts with whom the first user authorizes sharing some or all of the health information without the need for additional user input when approaching the entrance of one of those personal contacts. For example, the first user can identify friends, family, businesses, and other personal contacts that the first user knows or may visit on a regular basis, each contact of which can be customized with sharing preferences. The first user can set the system software to automatically share information to those selected contacts (e.g., "known" contacts) when the first computing device is detected at the entry of one of those contacts. For example, the software is set to authorize sharing vaccination status and current body temperature to close friends and family members; for other system users, the software is set to prompt the first user for input to grant authorization to share vaccination information or answers to a health questionnaire. The system software enables the second user (e.g., the homeowner, dwelling occupant, business) to ask the first computing device 552 for health information, send a health questionnaire to the first computing device 552, receive responses from the first computing device 552, and display notifications concerning information received (or not received). As will be appreciated, the first user may be a visitor in some instances and a building occupant who screens visitors in other instances, so the system software enables the user to share health information, request health information, communicate with other users via connected devices (e.g., video doorbell with audio and video), and communicate via messages and electronic communication.

Figure 12:
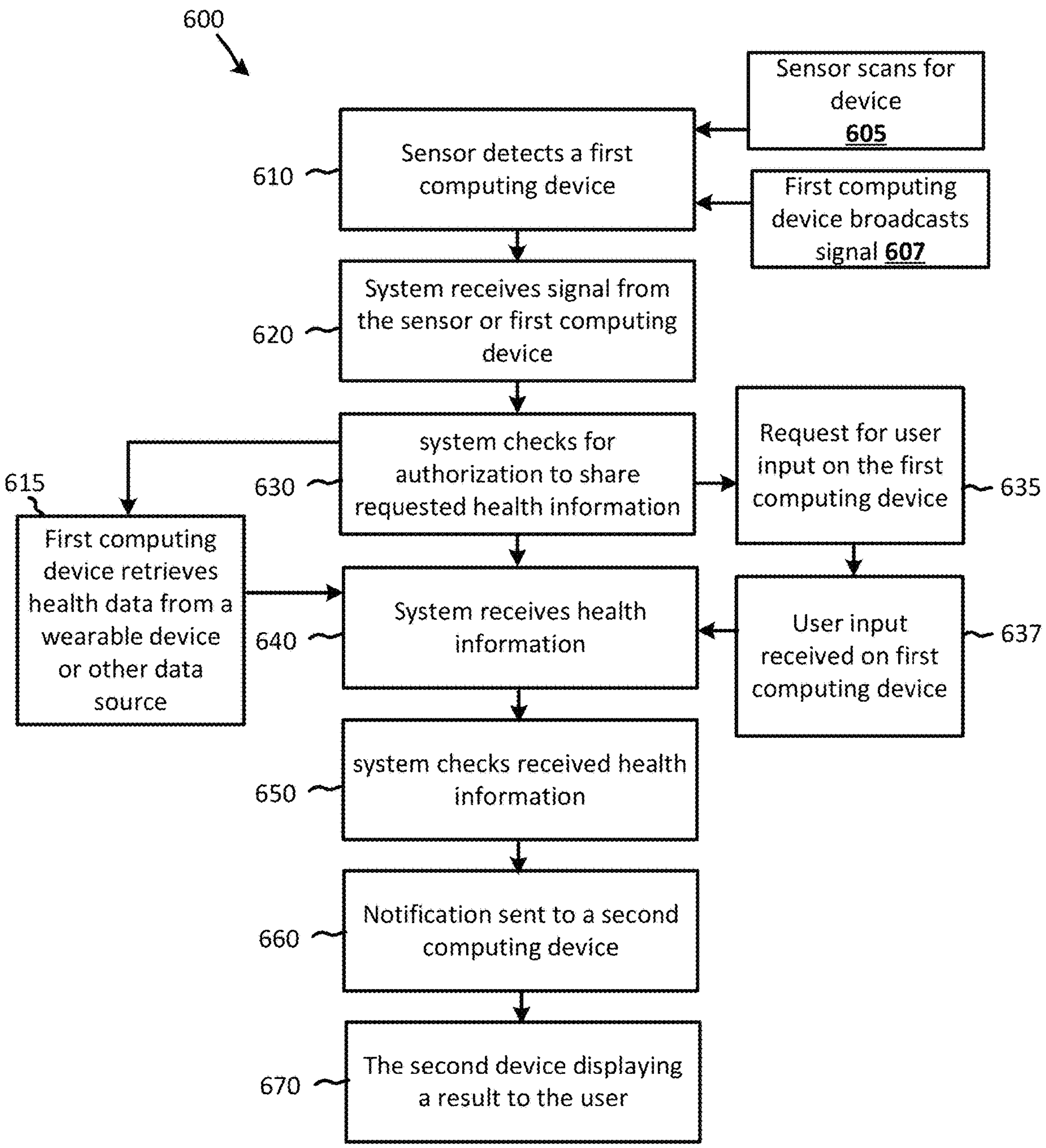
FIG. 12 illustrates a method of sharing health information, in accordance with an embodiment of the present disclosure.
Figure 13:
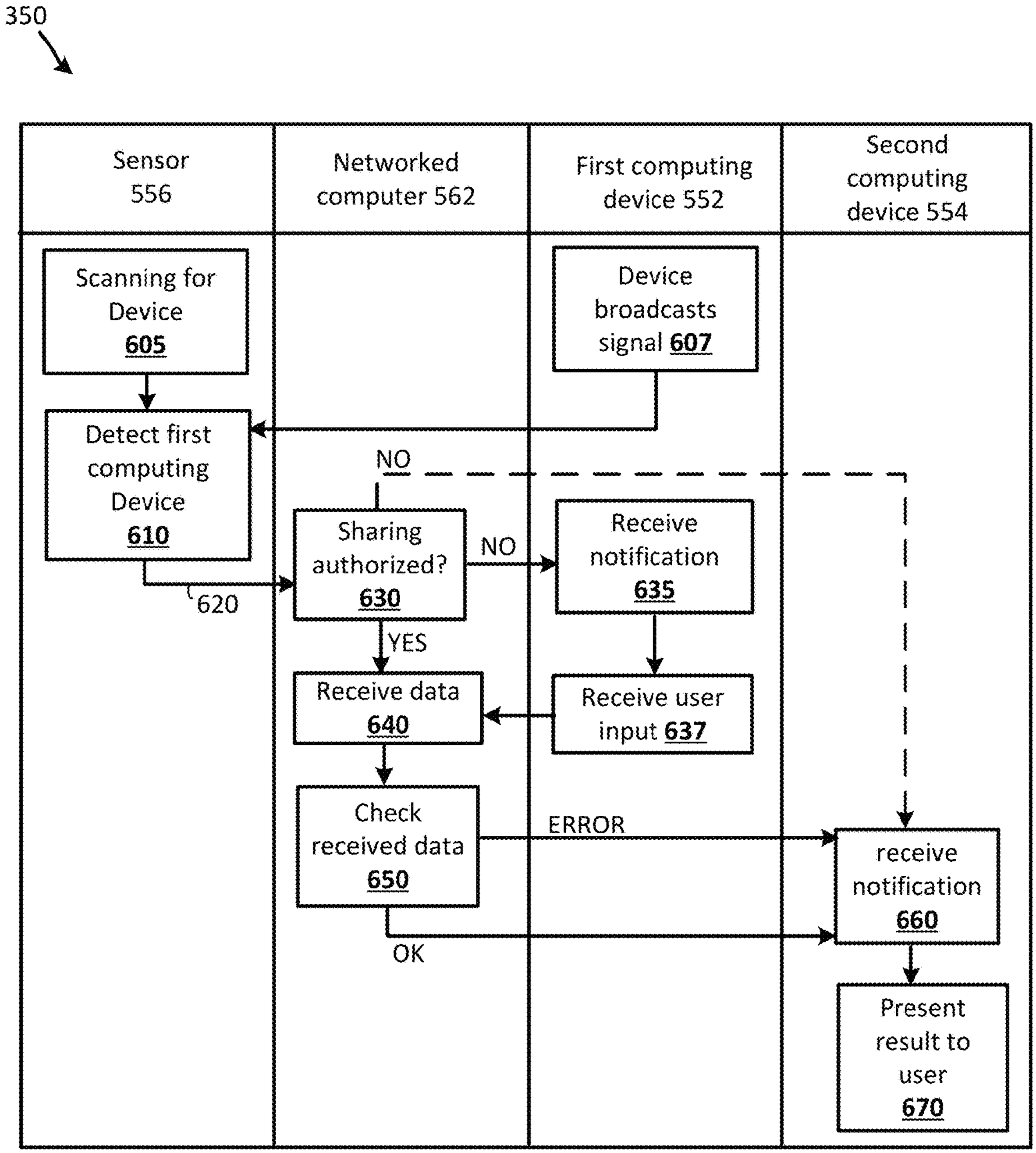
FIG. 13 is a diagram showing resource allocation for processes in a method of sharing health information of FIG. 12, in accordance with an embodiment of the present disclosure.

FIG. 12 illustrates a method 600 of sharing health information, in accordance with an embodiment of the present disclosure. FIG. 13 illustrates processes of method 600 as they may be performed by components of system 550. FIGS. 12-13 are discussed concurrently below.

Method 600 begins by the system detecting 610 a first computing device within range of the sensor, where the sensor is located adjacent a building entrance. As the first user approaches the entry, for example, the sensor receives a signal from the user's first computing device 552. In some embodiments, detecting 610 the first computing device includes the sensor scanning 605 for a device. For example, the sensor transmits an RF ping that is received by the first computing device. In another example, detecting 610 the first computing device can include the first computing device broadcasting 607 a signal that is received by the sensor. In another example, detecting 610 the first computing device includes the sensor detecting movement, sound, a change in light, a change in temperature profile, or other change in condition. In yet another example, detecting 610 the first computing device is performed by the user pressing a button on a doorbell assembly. In yet another example, detecting 610 the first computing device includes the sensor and first computing device "seeing" one another using a wireless communication protocol (e.g., RFID, Bluetooth, Wi-Fi, near-field communication) and communication between software running on the respective devices. Numerous variations and embodiments will be apparent in light of the present disclosure.

Method 600 continues with a networked computer receiving 620 a signal or notification from the sensor or from the first computing device, indicating the presence of a compatible device at the entry. In some embodiments, the signal from the first computing device indicates whether the device is authorized to share information. The networked computer (e.g., cloud-based computer) can communicate with the first computing device and with a second computing device (e.g., the homeowner's phone or tablet) using Wi-Fi or cell connection, where the second computing device also operates system software configured to perform processes in method 600. For example, the networked computer is a cloud computer in communication with the sensor and the user computing devices via Wi-Fi or cell service. In another example, the networked computer is a computer in the building sought to be entered and communicates with the sensor using a wired or wireless connection. In one such embodiment, the networked computer is a network hub or connected device of a smart home system.

Method 600 continues with the system checking 630 whether the first computing device is authorized to share or has provided health information that is requested by the second computing device (e.g., homeowner's phone). In one embodiment, the first computing device is configured to automatically share certain health information when encountering an entry that is part of the system and identified as a contact on the first computing device. For example, system software running on the sensor communicates with system software running on the first computing device and checks share settings on the first computing device.

If sharing is authorized, the system receives 640 health information from the first computing device and/or from some other source. Receiving 640 health information can include the networked computer receiving health data from the first computing device. Receiving 460 health information can include an optical camera of the system reading a 2D barcode displayed on the first computing device. Receiving 640 health information can include the networked computer acquiring stored health information from a third-party database. In other embodiments, receiving 640 data includes receiving health data acquired 615 by the first computing device from a wearable device of the first user, such as a smart watch or a fitness tracker. In one such embodiment, the system software is configured to cooperate with the wearable device using an application programming interface (API) to push or pull data from the wearable device to the first computing device. For instance, data of the wearable device is part of the health information that can be selected by the user to share, whether automatically, one-time, or for selected recipients. The data from the wearable device can include one or more of body temperature, skin temperature, pulse rate, and blood pressure, whether provided periodically, in real time, or upon request by the first computing device. In one example, the system software on the first computing device receives 615 data from the wearable device in response to the system checking 630 for authorization to share requested health information or in response to user input received 637 at the first computing device. In some embodiments, health data is communicated directly from the first computing device to the second computing device, such as by peer-to-peer sharing.

Method 600 continues with the system checking 650 the received data. In one embodiment, checking the received data 650 includes comparing the type and quality of the received data, such as whether the shared health information is the same type as that requested by the second computing device (e.g., homeowner's phone or tablet) and whether the value of that data meets the criteria set by the second computing device. For instance, the networked computer compares the second computing device's requested information with the information available or received from the first computing device. In one example, the second computing device is configured to request vaccination status and body temperature of the user of the first computing device; the first computing device is configured to automatically share body temperature, but it does not authorize sharing vaccination status. In such case, the system identifies a mismatch between the type and/or amount of information sought and the information provided. For items of health information that satisfy the second computing device's request, the system determines whether the data (e.g., body temperature) is within the acceptable range specified by the second computing device. In some embodiments, checking 650 received data includes determining that the user declines to share health information or that no response has been received from the first computing device.

In some embodiments, when requested data is not pre-authorized to be shared by the first computing device, method 600 may proceed with the system (e.g., the networked computer) sending 635 a notification to the first computing device with a request for user input. The notification can be a request to share the stored vaccination information (e.g., authorization to transmit), a request to complete a questionnaire, request to update software configuration, or some other request for user input. The notification may be a push notification, for example.

The first user can respond to the notification provided in process 635 by providing user input, which is received 637 on the first computing device. For example, the user can touch a button, answer one or more questions, or decline to share.

User input received 637 on the first computing device can result in the system (e.g., the networked computer) receiving 640 data from the first computing device, the networked computer acquiring stored health information from a third-party database, or a combination of thereof. In one example, the received data includes answers to a health screening questionnaire, health data obtained from a wearable device, or the requested health information (e.g., vaccination status). In another example, the received data is an authorization for the networked computer to acquire stored health information from the third-party database, such as an employer database or health practitioner database.

In another example, receiving 640 data includes an optical camera capturing an image of a 2D barcode (e.g., a QR code) displayed on the first computing device, and the system (e.g., the networked computer or processor coupled to the optical camera) processing the 2D barcode to determine its contents. In one such embodiment, the 2D barcode is processed by the networked computer to access health data stored on a remote computer. Upon the networked computer receiving 640 data, the networked computer checks 650 whether the received data satisfies the requested health information, as discussed above.

When health information or other data is received 640 from the first computing device, method 600 proceeds with the networked computer checking the received health information and sending 660 a notification to the second computing device. In some embodiments, the notification is a push notification from the networked computer. In one example, the notification indicates that the requested health information is not provided or not available. In other embodiments, the notification includes the requested health data or results of the request.

Method 600 continues with the second computing device displaying or otherwise presenting 670 a result to the user. The presented result, for example, can be a visual indication and/or an audible indication, and can indicate compliance or non-compliance with one or more component of the requested health information, or the result can be a more detailed account of health information received by the system. For example, the second computing device displays the result as a green check mark (or red X) to indicate that the user of the first computing device satisfies (or does not satisfy) the health criteria asked by the user of the second computing device. The second computing device optionally sounds an audible alert in conjunction with presenting a visual display. In another example, a smart speaker presents an audible result (e.g., "visitor's health status is OK"). In another example, the second computing device displays answers to a questionnaire completed by the user of the first computing device. In another example, the displayed result shows a summary of health data, such as vaccination status and current body temperature. In another example, the displayed result indicates which data meets and does not meet the requested criteria of the second computing device. In another example, the displayed result indicates that the requested health information is not available or that the user declined to share it. Numerous variations and embodiments will be apparent in light of the present disclosure.

In use, system 550 a building occupant can screen visitors at an entrance of the building by enabling the visitor to share, and the building occupant to review, health information of the visitor from one device to another.

Figure 14:
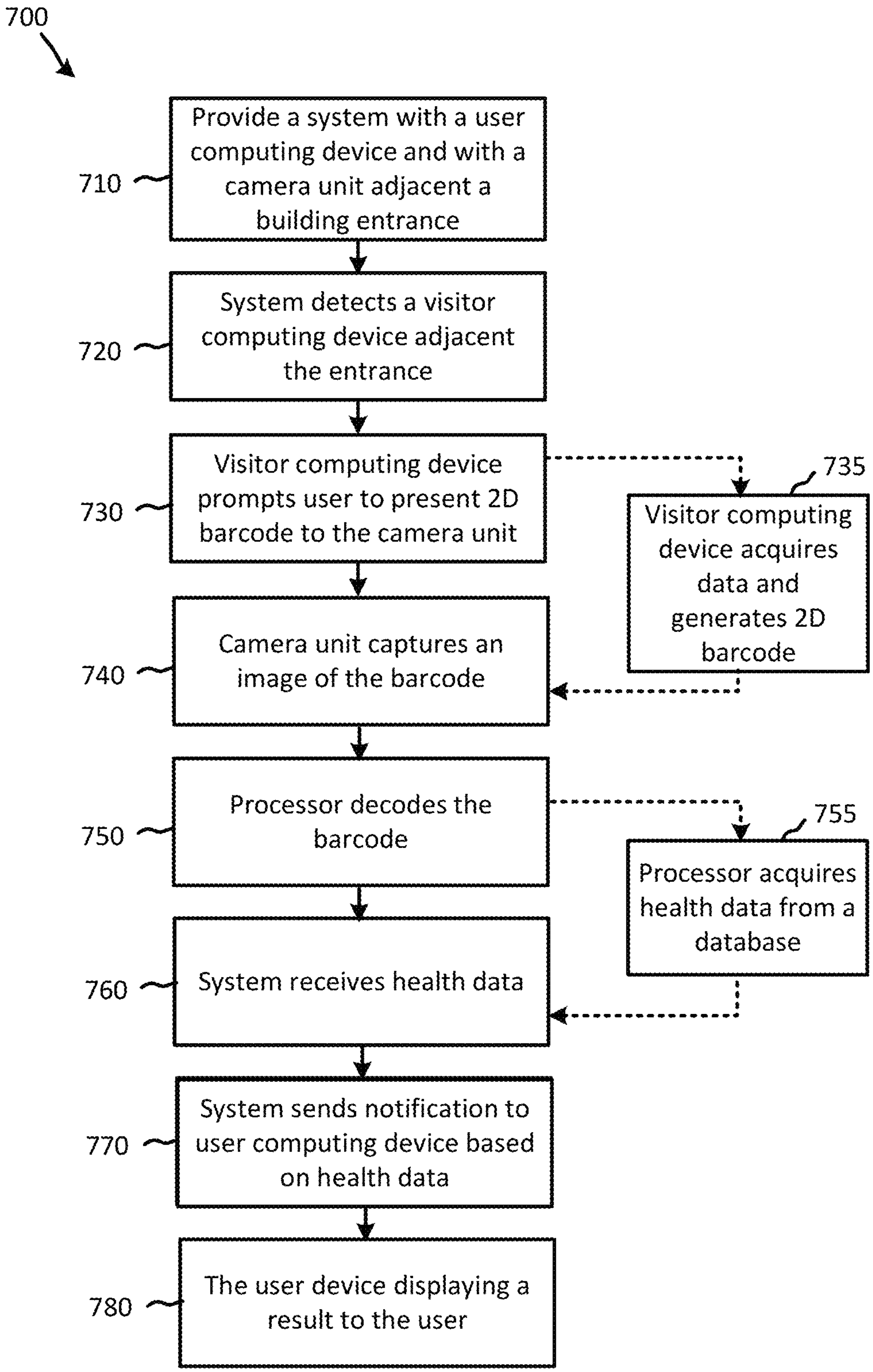
FIG. 14 illustrates a method of sharing health information, in accordance with another embodiment of the present disclosure.

Referring now to FIG. 14, a flowchart illustrates a method 700 of sharing health data, in accordance with another embodiment of the present disclosure. Method 700 utilizes data presented in the form of a 2D barcode on a visitor's computing device (e.g., mobile phone) or transmitted in encrypted form from visitor's computing device. A sensor acquires an image of the 2D barcode and the system processes the 2D barcode to extract its contents. Method 700 is discussed in more detail below. Although method 700 is discussed in the context of a 2D barcode, method 700 could similarly use encrypted health data that is communicated from the visitor's computing device to the user's computing device directly (e.g., via peer-to-peer sharing) or indirectly (e.g., via a smart home network or local area network).

Method 700 begins with providing 710 a system that includes a user computing device, a camera unit positioned adjacent a building entrance, and a visitor computing device. For example, the system is a smart home system or a home Wi-Fi network in which various devices can communicate with one another via wireless communication, such as Wi-Fi or Bluetooth. The user computing device can be a mobile phone, a television, a smart display, a home computer, a smart speaker, or other networked device in communication with the optical camera. The camera unit can be a standalone outdoor optical camera unit in a housing mounted near a building entrance, such as near a doorbell, an optical camera that is part of a non-contact body temperature system as discussed above, an optical camera of a video-doorbell or smart-home security system, a barcode reader or other reader for machine-readable data, or an outside home camera, to name a few examples. Regardless of its configuration, the camera unit has the ability to acquire an image of and/or scan a 2D barcode and communicate the 2D barcode (or information contained therein) to another computing device (e.g., the user's computing device) either directly or indirectly (e.g., via a network hub or server). An example of a camera unit is shown in FIGS. 1-2 and discussed above. An example of an optical camera is also shown in FIG. 3. The visitor's computing device can be a mobile computer, such as a tablet computer, laptop computer, a smart phone, a smart watch, or other portable computing device. The visitor's computing device includes stored health data, such as vaccination status, a stored health questionnaire, or other health information, that can be presented in the form of a 2D barcode.

Method 700 continues with the system detecting 720 the visitor's computing device. As discussed above, detecting 720 can include wireless communication between software on the visitor's computing device and software on the camera unit, RF communication, or detection by some other means.

Method 700 continues with prompting 730 the visitor to present health data in the form of a 2D barcode in the field of view of the camera unit. For example, after detecting 720 the presence of the visitor's computing device, the system communicates with the visitor's computing device and prompts the user to position the display in the field of view of the optical camera while the system software on the visitor's device displays a 2D barcode containing health data.

Optionally, the visitor computing device acquires health data from a wearable device and/or other source, and generates 735 a 2D barcode containing the data. For example, in combination with prompting 730 the user, the system software on the visitor's computing device acquires data from a smart watch or other wearable device, the data including body temperature, pulse rate, blood pressure, or other health data. The visitor computing device generates 735 a 2D barcode containing the acquired health data.

Method 700 continues with the camera unit capturing 740 an image of the 2D barcode, followed by a processor processing 750 the barcode to extract the data. In some embodiments, the 2D barcode includes health information, such as one or more of a vaccination record, a health credential, a body temperature (e.g., acquired by the visitor's computing device from a wearable device), authorization to access data stored on a remote database, or other health data. Optionally, the 2D barcode includes a link to and authorization for the system to acquire health data from a third-party database, such as a health insurance portal or medical practitioner database.

Method 700 continues with the system receiving 760 health data. In some embodiments, receiving 760 health data can include one or more of receiving data via the camera unit, receiving data communicated from the visitor computing device to a system device (e.g., network hub or user computing device), or the system acquiring health data from a database linked by the 2D barcode.

Method 700 continues with sending 770 a notification to the user computing device based on the acquired health data, and the user computing device displaying 770 a result to the user.

FIGS. 15A-15G illustrate examples of a graphical user interface 162 at various stages of methods 600 and 700 as displayed on a mobile phone, in accordance with some embodiments. The graphical user interface 162 can be formatted for display on other devices, such as a tablet computer, desktop computer, smart display, television, or other electronic device.

Figure 15A:
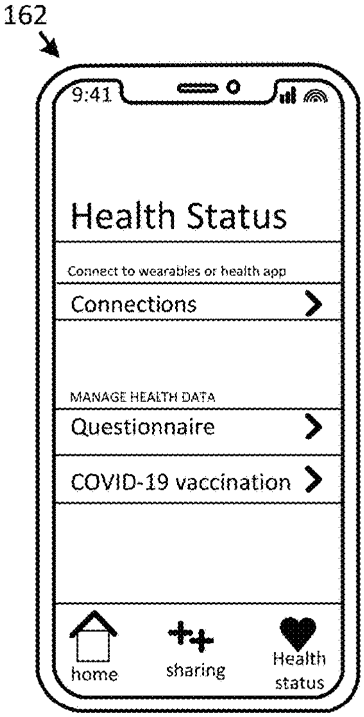
FIGS. 15A-15L illustrate examples of a graphical user interface at various stages of a method of sharing health information, in accordance with some embodiments.

FIG. 15A illustrates a graphical user interface 162 showing a health status screen where the user can add connections and manage health data. The device user can choose what health information to share with others. In this example, the health status screen is presented in the context of the user being a visitor and includes menus for the user to add connections and to select preferences for health information. Health information can be stored on the computing device (e.g., a phone or tablet), can be acquired from wearable devices (e.g., a fitness tracker or smart watch), can be input by the user, or can be from a combination of these and other sources.

Figure 15B:
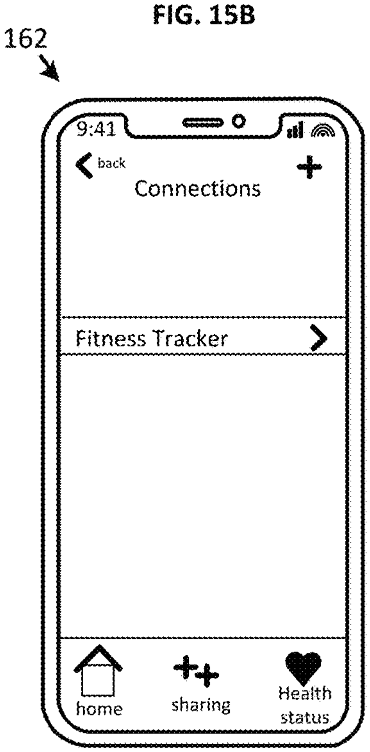

FIG. 15B illustrates a connections screen of a graphical user interface 162. In this example, the user can add connections to other system devices, such as a wearable device. A plurality of device and application connections can be made, including communication with wearable devices and access to data via other software applications. In this example, the user can press the 'plus' sign in the upper right corner of the graphical user interface 162 to add a new connection. "Fitness tracker" is shown as an existing connection and includes an arrow for the user to access additional information about this connection.

Figure 15C:
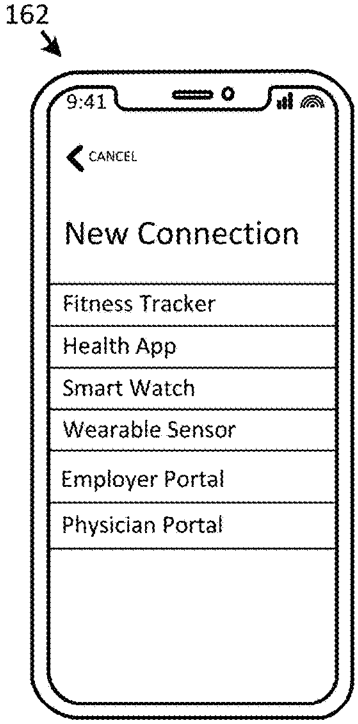

FIG. 15C illustrates a new connection screen of a graphical user interface 162. In this example, the graphical user interface 162 shows a list of supported devices and software applications. The user can select from the list to add and configure a connection. In this example, possible new connections include a fitness tracker, a health app, a smart watch, a wearable sensor, an employer portal, and a physician portal.

Figure 15D:
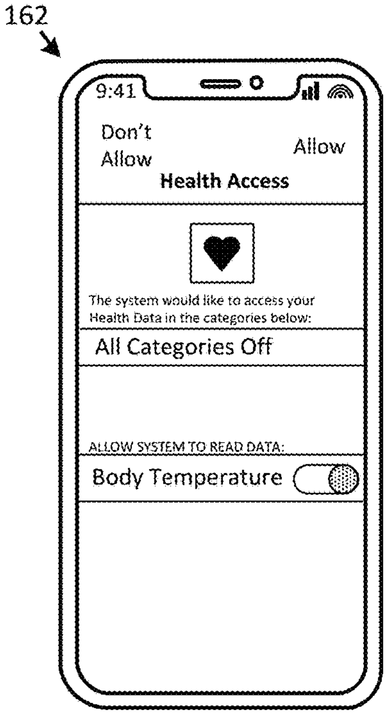

FIG. 15D illustrates a permissions screen of a graphical user interface 162. In this example, the graphical user interface 162 prompts the user for authorization for the system software to share health information with a requesting device, such as a homeowner's computing device or sensor unit that is part of a smart home network.

Figure 15E:
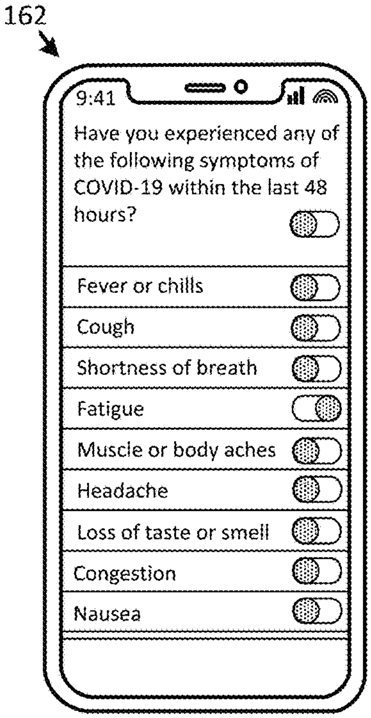

FIG. 15E illustrates a graphical user interface 162 with an example of a health questionnaire presented to the user (visitor) after the first computing device is prompted to display the questionnaire. In this example, the questionnaire is configured for symptoms of COVID-19; other health questions can be used, as will be appreciated. The user may use a slider at the top of the questionnaire to indicate YES to experiencing any one or more listed symptoms. Additionally, or in the alternative, the user can use sliders to answer each symptom individually. In some embodiments, the questionnaire is stored on the visitor's computing device. In other embodiments, the questionnaire is transmitted from the building occupant's computing device or from the system to the visitor's computing device.

Figure 15F:
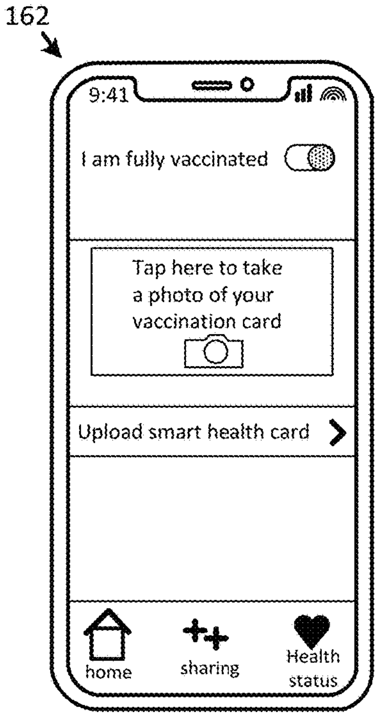

FIG. 15F illustrates a graphical user interface 162 with a vaccination status screen. In this example, the user can self-report whether the user is fully vaccinated using a slider. Additionally, the user can use the phone's camera to capture an image of a vaccination card or the like. In some embodiments, a digital proof of vaccination or other support document can be saved to the device and accessed by the system software. In some embodiments, the graphical user interface 162 includes a button to upload a smart health card.

Figure 15G:
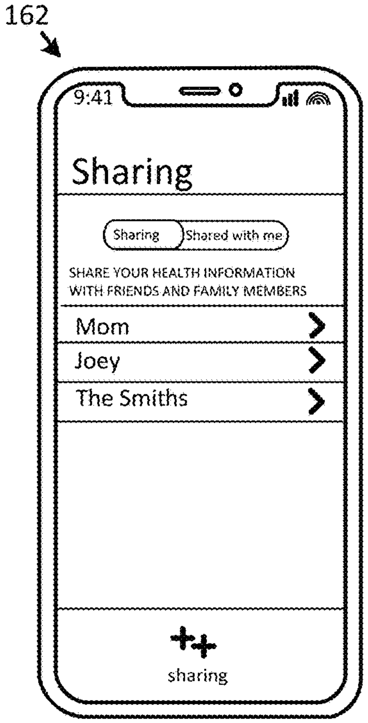

FIG. 15G illustrates a graphical user interface 162 showing a sharing screen. In this example, the device user can select and add individuals or establishments with whom the user wishes to pre-authorize sharing of health information. In this example, the user has Mom, Joey, and The Smiths as personal contacts with whom the user can pre-authorize sharing of some or all of the user's health information as deemed appropriate. When the user approaches the entrance to any one of these personal contacts, the system software is pre-configured to allow sharing health information with that particular contact as established by the user in the software preferences.

Figure 15H:
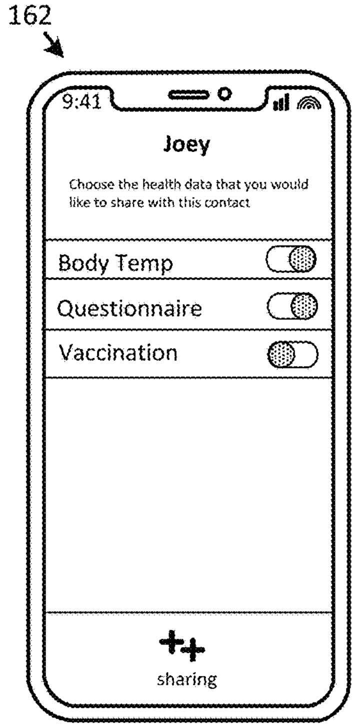

FIG. 15H illustrates an example graphical user interface 162 showing details of shared information for a given personal contact. In this example, the user has selected to automatically share body temperature and a screening questionnaire with another system user, Joey. When the user approaches Joey's entrance, for example, the user's device (e.g., visitor or first computing device 552) shares body temperature and questionnaire data with Joey via his device (e.g., user or second computing device 554). Joey will receive an alert on his device informing him of the current health status of the user, for example.

Figure 15I:
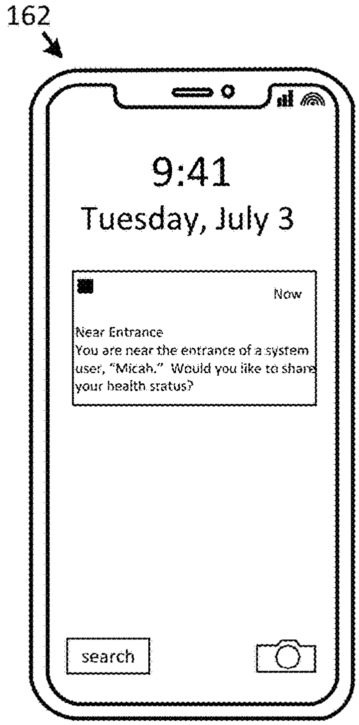

FIG. 15I illustrates an example of a graphical user interface 162 showing an alert on the building occupant's device (e.g., second computing device 554. In this example, the first or visitor computing device displays an alert to the user (e.g., visitor) that the user is approaching Mica's entrance, and prompts the user for authorization to share health information. In this example, the user has not established sharing preferences for Micah, so the first computing device requires user input from the user before sharing the health information. In other embodiments where the user has set up sharing authorizations, the system software of the visitor/user's device (e.g., first computing device) may be pre-authorized to share health information and no user input is required. For example, the user of the first computing device (e.g., visitor) may receive an alert confirming that health data has been shared.

Figure 15J:
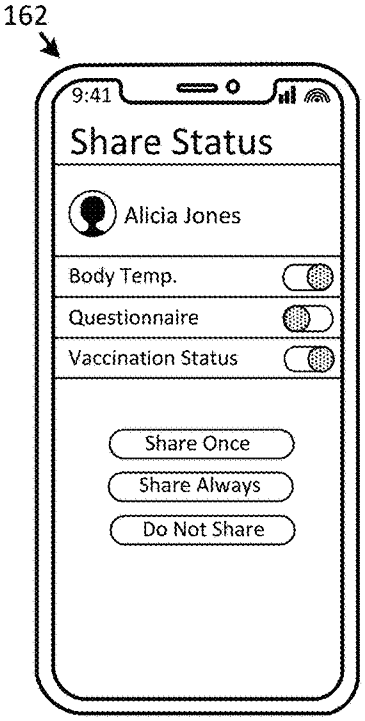

FIG. 15J illustrates a graphical user interface 162 showing share status of a new personal contact. In this example, the user has pre-authorized the device to share body temperature and vaccination status with a personal contact, Alicia Jones. The user can use buttons to select "share once," "share always," or "do not share" as deemed appropriate by the user. The user can also determine if the personal contact, Alicia Jones, is added to a sharing list.

Figure 15K:
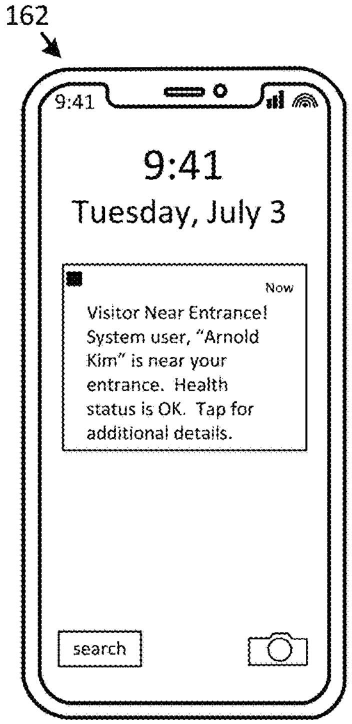

FIG. 15K illustrates a graphical user interface 162 showing a notification with summary of results displayed on the device of a homeowner or other building occupant (e.g., on the second computing device 554) when the visitor authorizes sharing health information, either in advance or upon being prompted to do so. In this example, the notification informs the user (e.g., building occupant) that a visitor and system user, Arnold Kim, is near the entrance, that health information of Arnold Kim has been shared and is confirmed to be OK. The notification provides the option for the user to tap the display for additional details.

Figure 15L:
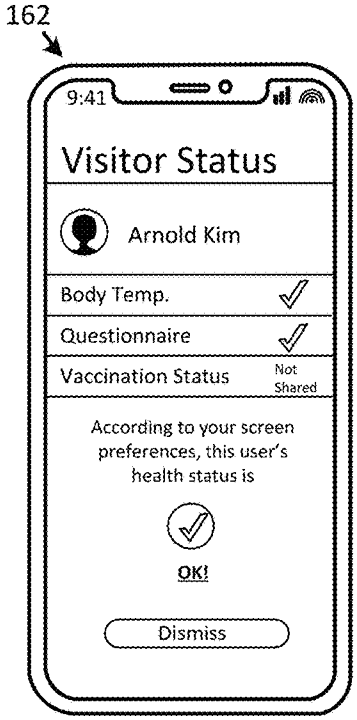

FIG. 15L illustrates a graphical user interface 162 showing details of results displayed to the user (e.g., building occupant). In this example, the user receiving the notification shown in FIG. 14K has tapped the notification to see more details. The additional details in FIG. 14L show that Arnold Kim shared body temperature and answered and/or shared a screening questionnaire. Indicated by various check marks, the graphical user interface 162 also shows that this data individually and collectively satisfies the requirements established in the system software by the building occupant. The graphical user interface 162 further indicates that Arnold Kim did not share vaccination status. The user may touch "dismiss" to close the notification.

Figure 16:
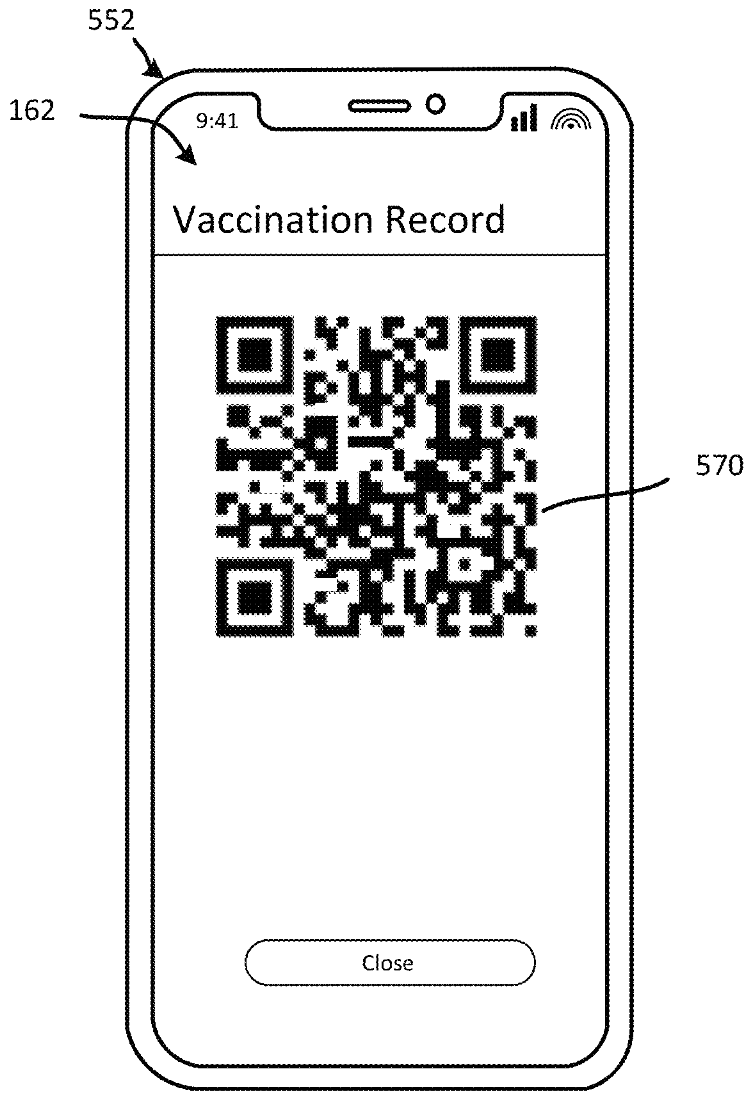
FIG. 16 illustrates an example of a user interface on a computing device that displays a 2D barcode containing health information.

FIG. 16 illustrates an example of a graphical user interface 162 of a visitor or first computing device 552 displaying a 2D barcode 570. In this example, the 2D barcode 570 includes health information, such as vaccination information or other encoded health information. The 2D barcode can be read by a sensor unit, such as a doorbell assembly 110 equipped with an optical camera 133 or other camera unit.

Further Example Embodiments

The following examples pertain to further embodiments, from which numerous permutations and configurations will be apparent.

Example 1 is a method comprising detecting a first computing device by a sensor unit adjacent a building entrance; requesting, by the sensor unit, health data from the first computing device; checking, by the first computing device, a configuration on the first computing device for authorization to share the health data with a user associated with the sensor unit; sending, by the first computing device, health data to a second computing device, if authorized to share the health data; receiving, by the second computing device, the health data from the first computing device; and notifying a user of the second computing device based on health data received from the first computing device.

Example 2 includes the subject matter of Example 1, wherein detecting the first computing device comprises the first computing device broadcasting a signal; and the sensor unit receiving the signal broadcast from the first computing device.

Example 3 includes the subject matter of Example 1, wherein detecting the first computing device comprises the sensor unit broadcasting a signal; the first computing device receiving the signal; and the first computing device communicating with the sensor unit in response to receiving the signal.

Example 4 includes the subject matter of any one of Examples 1-3, and further comprises the sensor unit sending a notification to a second computing device in response to detecting the first computing device; and the second computing device notifying a user about the presence of the first computing device at the building entrance.

Example 5 includes the subject matter of any one of Examples 1-4 and further comprises the first computing device prompting a user for input; and the first computing device receiving the input from the user, the user input including authorization or denial to share the health data with the user associated with the sensor unit.

Example 6 includes the subject matter of any one of Examples 1-5, wherein the health data pertains to a user of the first computing device and includes one or more of answers to a health screening questionnaire, a health certificate, a vaccination status, a proof of vaccination, and a biological measurement of the user of the first computing device.

Example 7 includes the subject matter of Example 6, wherein the biological measurement includes at least one of a body temperature, a pulse rate, and a blood pressure.

Example 8 includes the subject matter of Example 6, wherein the health certificate includes a self-reported certification.

Example 9 includes the subject matter of Example 6, wherein the health data includes the health screening questionnaire and the method further comprising the first computing device receiving the health screening questionnaire from the second computing device.

Example 10 includes the subject matter of Example 6, wherein the health data includes the health screening questionnaire and the health screening questionnaire stored on the first computing device, and the method further comprises the first computing device sending the health screening questionnaire to the second computing device.

Example 11 includes the subject matter of any one of Examples 6-10, wherein the health data is stored, at least in part, on the first computing device.

Example 12 includes the subject matter of any one of Examples 6-10, wherein the health data is stored, at least in part, in a remote database accessible via the Internet, the method further comprising: the first computing device acquiring the health data from the remote database; and the first computing device sending the health data to the sensor unit.

Example 13 includes the subject matter of any one of Examples 6-10, wherein the health data, at least in part, is received by the first computing device from a wearable device of a user of the first computing device.

Example 14 includes the subject matter of any one of Examples 6-10, wherein the health data, at least in part, is acquired by the first computing device from a health app on the first computing device.

Example 15 is a method of sharing health information among users of a system that includes a first computing device, a network computer, a second computing device, and a sensor unit, the method comprising detecting, by the sensor unit, a first computing device adjacent a building entrance; requesting, by the sensor unit, health information from the first computing device, the health information to be shared with a user of the second computing device and pertaining to a user of the first computing device; the network computer sending a notification to a second computing device based on health information received from the first computing device; and the second computing device notifying the user of the second computing device based on a comparison of the health information received and health information requested.

Example 16 includes the subject matter of Example 15, wherein detecting the first computing device comprises the first computing device broadcasting a signal; and the sensor unit receiving the signal broadcast from the first computing device.

Example 17 includes the subject matter of Example 15, wherein detecting the first computing device comprises the sensor unit broadcasting a signal; the first computing device receiving the signal; and the first computing device communicating with the sensor unit in response to receiving the signal.

Example 18 includes the subject matter of any one of Examples 15-17 and further comprises receiving, by the network computer, a signal from the sensor unit or from the first computing device in response to the sensor unit detecting the first computing device; and the second computing device notifying the user of the second computing device about the presence of the first computing device adjacent the building entrance.

Example 19 includes the subject matter of any one of Examples 15-18 and further comprises the network computer checking a local configuration on the first computing device for authorization to share the health information with the user of the second computing device.

Example 20 includes the subject matter of Examples 19 and further comprises the network computer sending a notification to the first computing device, if sharing is not authorized, the notification including a request for user input; the first computing device receiving the user input; and the network computer receiving the health information from the first computing device in response to the user input.

Example 21 includes the subject matter of any one of Examples 15-20, comprising the first computing device prompting a user for input; and the first computing device receiving the input from the user, the user input including authorization or denial to share the health data.

Example 22 includes the subject matter of any one of Examples 15-21, wherein the health information includes one or more of answers to a health screening questionnaire, a health certificate, a vaccination status, a proof of vaccination, and a biological measurement of the user of the first computing device.

Example 23 includes the subject matter of Example 22, wherein the biological measurement includes at least one of a body temperature, a pulse rate, and a blood pressure.

Example 24 includes the subject matter of Example 22, wherein the health certificate includes a self-reported certification.

Example 25 includes the subject matter of Example 22, wherein the health information includes the health screening questionnaire and the method further comprising the first computing device receiving the health screening questionnaire from the second computing device.

Example 26 includes the subject matter of Example 22, wherein the health information includes the health screening questionnaire and the health screening questionnaire is stored on the first computing device, and the method further comprises the first computing device sending the health screening questionnaire to the second computing device.

Example 27 includes the subject matter of any one of Examples 22-26, wherein the health information is stored, at least in part, on the first computing device.

Example 28 includes the subject matter of any one of Examples 22-26, wherein the health information is stored, at least in part, in a remote database accessible via the Internet, the method further comprising the first computing device acquiring the health data from the remote database; and the first computing device sending the health data to the sensor unit.

Example 29 includes the subject matter of any one of Examples 22-26, wherein the health information, at least in part, is received by the first computing device from a wearable device of the user of the first computing device.

Example 30 includes the subject matter of any one of Examples 22-26, wherein the health information, at least in part, is acquired by the first computing device from a health app on the first computing device.

Example 31 is a method for a smart home network, the method comprising a doorbell assembly detecting a visitor to the door; the doorbell assembly prompting the visitor to display a machine-readable code using a first computing device; an outdoor camera connected to the smart home network reading the machine-readable code from the first computing device, the machine-readable code containing health data of the visitor; a network computer of the smart home network processing the machine-readable code; and a second computing device connected to the smart home network notifying a user of the smart home network based on health data of the visitor encoded in the machine-readable code.

Example 32 includes the subject matter of Example 31, wherein the doorbell assembly is a video doorbell assembly enabled to read the machine-readable code.

Example 33 includes the subject matter of Example 32, wherein the machine-readable code is a 2D barcode.

Example 34 includes the subject matter of any one of Examples 31-33, wherein the outdoor camera is part of the doorbell assembly or is a stand-alone camera unit connected to the smart home network.

Example 35 includes the subject matter of any one of Examples 31-34, wherein the second computing device is selected from a smart phone, a smart display, a computer, and a smart speaker.

Example 36 includes the subject matter of any one of Examples 31-35, wherein prompting the user is performed using a speaker and/or a graphical display of the doorbell assembly.

Example 37 includes the subject matter of any one of Examples 31-36, wherein prompting the visitor includes playing a pre-recorded message or displaying a message on a graphical user interface.

Example 38 includes the subject matter of any one of Examples 31-37, wherein the outdoor camera is part of the doorbell assembly, part of a security system, an add-on accessory to the doorbell assembly, a stand-alone camera accessory.

Example 39 includes the subject matter of any one of Examples 31-38, wherein the second computing device includes a graphical user interface, the method further comprising the doorbell assembly forwarding the machine-readable code to the network computer and the computer forwarding decoded health data to the second computing device.

Example 40 includes the subject matter of any one of Examples 31-39, wherein detecting the visitor comprises at least one of actuation of the doorbell assembly, detecting a motion of the visitor, and communication between the first computing device and the smart home network.

Example 41 includes the subject matter of any one of Examples 31-40, wherein the health data includes one or more of answers to a health screening questionnaire saved on the first computing device, a vaccination status, a proof of vaccination, a biological measurement of the visitor acquired from a wearable electronic device disposed in communication with the first computing device, a biological measurement of the visitor acquired from a health app on the first computing device, health information of the visitor acquired from a remote database accessible via the Internet.

Example 42 is a system configured to perform a method of any of Examples 1-41.

Example 43 is a system for non-contact body temperature determination of a visitor at a building entrance equipped with a doorbell, the system comprising a doorbell for a building entrance, the doorbell actuatable by a visitor; a temperature sensor unit configured to be mounted adjacent the building entrance and configured to wirelessly transmit a signal, the temperature sensor unit responsive to actuation of the doorbell, wherein the temperature sensor unit includes a temperature sensor configured to acquire body temperature information of a human subject within a field of view of the temperature sensor; and a computing device having a user interface, the computing device configured to wirelessly communicate with the temperature sensor unit, to receive the body temperature information from the temperature sensor unit, and to display the body temperature information of the human subject to a user.

Example 44 includes the subject matter of Example 43, wherein the temperature sensor unit includes a first wireless transceiver; the doorbell is part of a doorbell assembly including a doorbell button, a microphone, a speaker, an optical camera, and a second wireless transceiver; and the computing device is further configured to display images captured by the optical camera.

Example 45 includes the subject matter of Example 43 or 44, and further comprises a network hub configured to enable wireless communication between any one or more of the temperature sensor unit, the computing device, and the doorbell assembly, wherein the computing device is configured to receive user input to control operation of one or both of the temperature sensor unit and the doorbell assembly.

Example 46 includes the subject matter of Example 44, further comprising a network hub configured to enable wireless communication between the temperature sensor unit and the doorbell assembly.

Example 47 includes the subject matter of any one of Examples 44-46, further comprising a server computer in communication with the computing device and with the temperature sensor unit, the server computer configured to process the body temperature information received from the temperature sensor unit and communicate processed temperature information to the computing device.

Example 48 includes the subject matter of any one of Examples 44-47, wherein the temperature sensor unit is configured to detect an audible chime of the doorbell assembly.

Example 49 includes the subject matter of any one of Examples 44-48, and further comprises a motion sensor disposed in communication with at least one of the doorbell assembly and the temperature sensor unit.

Example 50 includes the subject matter of any one of Examples 44-49, wherein the temperature sensor unit is further configured to determine ambient temperature.

Example 51 includes the subject matter of any one of Examples 44-50, and further comprises an optical camera on the temperature sensor unit.

Example 52 includes the subject matter of any one of Examples 44-51, wherein the wireless communication includes at least one of a Bluetooth communications protocol, near-field communication, Radio Frequency communication, and a Wi-Fi communications protocol.

Example 53 is a method of detecting a temperature of a visitor at a building entrance equipped with a doorbell, the method comprising providing a temperature sensor unit adjacent to the building entrance, the temperature sensor unit including a temperature sensor and a wireless communications transceiver; providing a computing device configured to wirelessly communicate with the temperature sensor unit; acquiring, by the temperature sensor unit, body temperature data of the visitor; communicating, by the temperature sensor unit, the body temperature data to the computing device via the wireless communications transceiver; and displaying, by the computing device, a body temperature of the visitor to a user.

Example 54 includes the subject matter of Example 53, and further comprises detecting, by the temperature sensor unit or the doorbell, a visitor at the building entrance.

Example 55 includes the subject matter of Example 54, wherein detecting the visitor at the building entrance includes the temperature sensor unit detecting an audible chime of the doorbell.

Example 56 includes the subject matter of Example 53, wherein detecting the visitor is performed by a motion detector in communication with the temperature sensor unit.

Example 57 includes the subject matter of Example 54, wherein the doorbell is a video doorbell and detecting the visitor at the building entrance includes receiving a signal from the video doorbell.

Example 58 includes the subject matter of any one of Examples 53-57, and further comprises the computing device notifying the user of a visitor at the building entrance; prompting the user for an input; receiving the input from the user; and in response to receiving the input, processing the body temperature data.

Example 59 includes the subject matter of any one of Examples 53-58, wherein acquiring the body temperature data of the visitor includes determining a facial region of the visitor and acquiring a thermal image including the facial region.

Example 60 includes the subject matter of any one of Examples 53-59, wherein displaying the body temperature of the visitor includes displaying a thermal image.

Example 61 includes the subject matter of any one of Examples 53-60, wherein the doorbell is part of a doorbell assembly comprising a doorbell button, an optical camera, a microphone, and a speaker, and wherein the method further comprises the doorbell assembly communicating a press of the doorbell button to the computing device; the computing device prompting the user to acquire the body temperature data; and in response to the computing device receiving user input, the temperature sensor unit acquiring the body temperature data.

Example 62 includes the subject matter of Example 62, and further comprises detecting, using the optical camera, a facial region of the visitor; and determining a body temperature of the visitor based on body temperature data of the facial region. The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more limitations as variously disclosed or otherwise demonstrated herein.

What is claimed is:

1. A method comprising:

providing a smart home system of network-enabled electronic devices disposed in wireless communication, the smart home system comprising an occupant computing device and a video doorbell assembly that includes a microphone, a speaker, and an optical camera at or adjacent to an entrance to a home, the optical camera configured to scan and read a machine-readable code;

prompting a user of a visitor computing device to generate and display a machine-readable code to the optical camera;

the optical camera reading the machine-readable code from the visitor computing device, the machine-readable code containing health data stored on the visitor computing device and pertaining to a user of the visitor computing device, wherein the health data includes one or more of a health certificate, a vaccination status, a vaccination record, and an identification;

processing, by the smart home system, the machine-readable code to provide processed health data; and providing, by the smart home system, a notification on the occupant computing device based on the processed health data.

2. The method of claim 1, wherein the health data comprises contemporaneous data acquired in real time from a wearable device or embedded microchip in communication with the visitor computing device.

3. The method of claim 1, wherein the machine-readable code further includes additional health data retrieved from a remote database via the Internet, the method further comprising:

comparing, by the smart home system, the additional health data with one or more stored criteria; and notifying, by the smart home system, the user of the occupant computing device based on comparison results of the additional health data with the one or more stored criteria.

4. The method of claim 1, further comprising enabling the optical camera to scan and read the machine-readable code.

5. The method of claim 1, wherein processing the machine-readable code includes communication with a server computer.

6. A method for a smart home network, the method comprising:

providing a smart home network including a plurality of network-enabled electronic devices disposed in wireless communication, the smart home network including a video doorbell assembly adjacent an exterior door of a residence and having a speaker, a microphone, and an optical camera, wherein the video doorbell assembly is configured to scan and read a machine-readable code;

detecting a visitor computing device adjacent the exterior door;

the video doorbell assembly establishing wireless communication with the visitor computing device in response to detecting the visitor computing device;

prompting, via the video doorbell assembly, the visitor to display a machine-readable code on the visitor computing device;

a component of the smart home network reading the machine-readable code displayed on the visitor computing device;

the smart home network processing the machine-readable code, the machine-readable code containing data pertaining to the visitor; and providing a notification, by the smart home network, based on a comparison between data contained in the machine-readable code and one or more stored criteria.

7. The method of claim 6, wherein the data pertaining to the visitor includes one or more of answers to a health screening questionnaire saved on the first computing device, a health certificate, a vaccination record, and a body temperature of the visitor.

8. The method of claim 6, further comprising enabling the video doorbell assembly to scan and read the machine-readable code.

9. The method of claim 6, further comprising receiving additional health data from a wearable device or an embedded microchip in communication with the visitor computing device.

10. The method of claim 6, wherein the component of the smart home network is the video doorbell assembly enabled to scan and read a machine-readable code.

11. The method of claim 6, wherein the data pertaining to the visitor includes a real-time body temperature of the visitor, wherein the body temperature originates from a wearable device or embedded microchip on the visitor.

12. A method of sharing health data among users of a smart home network having a video doorbell assembly adjacent an exterior door of a residence, wherein the video doorbell assembly is enabled to scan and read a machine-readable code and has a speaker, a microphone, and an optical camera, the method comprising:

a visitor computing device approaching the exterior door of the residence;

establishing, by the visitor computing device, wireless communication with the video doorbell assembly;

receiving, by the visitor computing device, a request from the smart home network;

acquiring, by the visitor computing device, real-time body temperature information from a wearable sensor disposed in communication with the visitor computing device;

generating, by the visitor computing device, a machine-readable code containing the real-time body temperature information; and displaying, using the visitor computing device, the machine-readable code to the optical camera of the video doorbell assembly.

13. The method of claim 12, comprising:

retrieving, by the visitor computing device, health data from a remote database via the internet, wherein the machine-readable code contains the health data retrieved from the remote database.

14. The method of claim 12, wherein the machine-readable code includes information stored on the visitor computing device.

15. The method of claim 12, wherein establishing wireless communication includes receiving, by the visitor computing device, a broadcast signal from the smart home network.

16. The method of claim 12, wherein establishing wireless communication is performed using near-field communication.

17. The method of claim 1 wherein the video doorbell assembly is a single unit housing the microphone, the speaker, and the optical camera, the single unit configured to be mounted adjacent to an exterior entrance of a home.

* * * * *